(12) United States Patent
Morrison et al.

(10) Patent No.: US 10,591,409 B2
(45) Date of Patent: Mar. 17, 2020

(54) SYSTEMS, DEVICES, AND METHODS FOR SAMPLE INTEGRITY VERIFICATION

(71) Applicant: Theranos, Inc., Palo Alto, CA (US)

(72) Inventors: Zachary Morrison, Palo Alto, CA (US); Daniel Young, Palo Alto, CA (US); Sunny Balwani, Palo Alto, CA (US); Michael Chen, Sunnyvale, CA (US)

(73) Assignee: Theranos IP Company, LLC, New York, NY (US)

( * ) Notice: Subject to any disclaimer, the term of this patent is extended or adjusted under 35 U.S.C. 154(b) by 0 days.

(21) Appl. No.: 15/250,530

(22) Filed: Aug. 29, 2016

(65) Prior Publication Data

US 2017/0131198 A1    May 11, 2017

Related U.S. Application Data

(63) Continuation-in-part of application No. 14/631,776, filed on Feb. 25, 2015, now abandoned, and a
(Continued)

(51) Int. Cl.
*G01N 21/03* (2006.01)
*G02B 21/06* (2006.01)
(Continued)

(52) U.S. Cl.
CPC ........... *G01N 21/03* (2013.01); *G02B 7/1821* (2013.01); *G02B 21/0004* (2013.01);
(Continued)

(58) Field of Classification Search
CPC ... G01N 2001/002; G01N 2035/00495; G01N 2035/00831; G01N 21/03;
(Continued)

(56) References Cited

U.S. PATENT DOCUMENTS

| 5,963,368 A | 10/1999 | Domanik et al. |
| 2006/0000296 A1* | 1/2006 | Salter ........................ B01L 9/06 |
| | | 73/863.01 |

(Continued)

FOREIGN PATENT DOCUMENTS

| EP | 2579026 A2 | 4/2013 |
| WO | 2011019576 A1 | 2/2011 |
| WO | 2014127379 A1 | 8/2014 |

OTHER PUBLICATIONS

International Search Report dated Dec. 29, 2016 for PCT/US2016/049133.
(Continued)

*Primary Examiner* — Francis Geroleo

(57) ABSTRACT

The devices, systems, and methods disclosed herein provide sample verification capabilities in a single device or system. Devices are disclosed herein. Systems including these devices are also provided. These devices and systems may be configured for verifying sample integrity prior to a subject leaving a sample collection site so that any further samples or other corrective action can occur without having to make a separate visit.

17 Claims, 15 Drawing Sheets

Related U.S. Application Data continuation-in-part of application No. 15/242,171, filed on Aug. 19, 2016, now Pat. No. 10,488,643, which is a continuation of application No. PCT/US2015/017581, filed on Feb. 25, 2015, application No. 15/250,530, which is a continuation-in-part of application No. PCT/US2016/049133, filed on Aug. 26, 2016.

(60) Provisional application No. 62/210,968, filed on Aug. 27, 2015, provisional application No. 62/237,527, filed on Oct. 5, 2015, provisional application No. 61/944,557, filed on Feb. 25, 2014.

(51) Int. Cl.

| | | |
|---|---|---|
| *G02B 7/182* | (2006.01) | |
| *G02B 21/36* | (2006.01) | |
| *G02B 21/34* | (2006.01) | |
| *G02B 21/00* | (2006.01) | |
| *G01N 35/00* | (2006.01) | |
| *G01N 1/00* | (2006.01) | |

(52) U.S. Cl.
CPC .............. *G02B 21/06* (2013.01); *G02B 21/34* (2013.01); *G02B 21/361* (2013.01); *G02B 21/362* (2013.01); *G02B 21/365* (2013.01); *G02B 21/367* (2013.01); *G01N 35/00663* (2013.01); *G01N 2001/002* (2013.01); *G01N 2035/00495* (2013.01); *G01N 2035/00831* (2013.01)

(58) Field of Classification Search
CPC .......... G01N 35/00663; G02B 21/0004; G02B 21/06; G02B 21/34; G02B 21/361; G02B 21/362; G02B 21/365; G02B 21/367; G02B 7/1821

See application file for complete search history.

(56) References Cited

U.S. PATENT DOCUMENTS

| | | |
|---|---|---|
| 2006/0184189 A1 | 8/2006 | Olson et al. |
| 2007/0016102 A1 | 1/2007 | Askin |
| 2007/0053794 A1 | 3/2007 | Perez et al. |
| 2007/0178580 A1 | 8/2007 | Tajima et al. |
| 2009/0048870 A1 | 2/2009 | Godshall et al. |
| 2010/0128165 A1 | 5/2010 | Newcomb et al. |
| 2010/0128256 A1 | 5/2010 | Thomson |
| 2011/0067490 A1* | 3/2011 | Walsh .................. G01F 23/292 73/149 |
| 2011/0226045 A1 | 9/2011 | McQuillan |
| 2012/0309030 A1 | 12/2012 | McKenna et al. |
| 2013/0024247 A1 | 1/2013 | Ausdenmoore et al. |
| 2013/0037564 A1* | 2/2013 | Williams ............... B01L 3/021 222/1 |
| 2013/0143257 A1 | 6/2013 | Small et al. |
| 2013/0175342 A1 | 7/2013 | Itoh |
| 2013/0293706 A1 | 11/2013 | Pison et al. |
| 2014/0020457 A1 | 1/2014 | Dayel et al. |
| 2014/0241945 A1 | 8/2014 | Oonuma et al. |
| 2015/0241684 A1 | 8/2015 | Morrison et al. |
| 2015/0316451 A1 | 11/2015 | Sercel et al. |
| 2017/0045729 A1 | 2/2017 | Morrison et al. |

OTHER PUBLICATIONS

Office Action dated Dec. 22, 2016 for U.S. Appl. No. 14/631,776.
International Search Report and Written Opinion dated Jul. 2, 2015 for PCT/US2015/017581.
CDC, OPRP-General Information on Hand Hygiene, Obtained from the Wayback Machine Mar. 29, 2012.
Office Action dated Jan. 14, 2019 for U.S. Appl. No. 15/242,171.
Office Action dated Nov. 5, 2018 for U.S. Appl. No. 15/292,063.
Office Action dated Feb. 1, 2019 for U.S. Appl. No. 14/631,776.
Office Action dated Apr. 18, 2018 for U.S. Appl. No. 15/242,171.
Office Action dated Jul. 11, 2017 for U.S. Appl. No. 14/631,776.
University of Utah (WebPath), Phlebotomy, Obtained from the Wayback Machine with Jan. 28, 2007 date.
Office Action dated Jun. 25, 2019 for U.S. Appl. No. 15/292,063.

* cited by examiner

SYSTEMS, DEVICES, AND METHODS FOR SAMPLE INTEGRITY VERIFICATION

CROSS-REFERENCE TO RELATED APPLICATIONS

This application claims priority to U.S. Provisional Patent Application Ser. No. 62/210,968 filed Aug. 27, 2015, U.S. Provisional Patent Application Ser. No. 62/237,527 filed Oct. 5, 2015, U.S. patent application Ser. No. 14/631,776 filed Feb. 25, 2015 which claims priority to U.S. Provisional Application Ser. No. 61/944,557 filed Feb. 25, 2015, and U.S. patent application Ser. No. 15/242,171 filed Aug. 19, 2016, which claims priority to PCT Application Ser. No. PCT/US15/17581 filed Feb. 25, 2015, which claims priority to U.S. Provisional Application Ser. No. 61/944,557 filed Feb. 25, 2014, the disclosures of which are all hereby fully incorporated by reference in their entirety for all purposes.

BACKGROUND

Analysis of biological samples from a subject may be important for health-related diagnosing, monitoring, or treating of the subject. A variety of methods are known for the analysis of biological samples. However, in order to provide better diagnosis, health monitoring, or medical treatment of subjects, it is desirable to also have a high quality sample or at least a minimum quality sample collected from the subject for analysis.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Applicants disclose herein multifunctional devices and systems. Using such devices and systems, measurements may be made, for example, on a biological sample, or on more than one biological sample. Optionally, some embodiments may take measurements from at least one biological and at least one non-biological object. Measurements made using multi-functional devices or systems disclosed herein, or made using methods disclosed herein, may further be made in concert with, or prior to, or following, other measurements made on the same biological sample or samples, or on a biological sample or samples derived from, obtained along with, or similar to, a biological sample or samples measured using the devices, systems, or methods disclosed herein.

In at least one embodiment, it is desirable to verify the sample collected from the subject for one or more sample characteristics before the subject has departed from the collection facility. In this manner if there are any issues with sample quality, sample integrity, sample volume, or any other characteristics, the issue(s) can be remedied without having to recall the subject from a location away from the collection facility. Optionally, the sample can be verified as part of the collection event, wherein the subject does not depart from the collection station until verification has occurred.

In at least one embodiment, the verification occurs in a device external to a sample imager. Optionally, some embodiments may include at least one processor in the sample imager that can verify the sample collected.

Accordingly, Applicants provide devices that are configurable for operation in one or more modes. One mode may be a sample verification mode of multiple characteristics. Other modes may be image capture mode, test mode, single characteristic verification mode, Applicants further provide systems comprising such devices. The configurations of systems disclosed herein may be changed, so that a system may be configured for operation in a spectroscopy mode at one time, and may be configured for operation in a fluorescence mode at another time, and may be configured for operation in a luminescence mode at yet another time.

In embodiments, such devices may comprise a sample container support such as but not limited to a sample container holder configured to hold a sample for observation, measurement, or analysis, e.g., for optical observation, measurement, or analysis. In embodiments, such devices may comprise a sample handling device configured to transport a sample, a sample holder, or both, to a location suitable for observation, measurement, or analysis, e.g., for optical observation, measurement, or analysis. In embodiments, a sample handling device may comprise a fluid handling device or system, or may be configured to operate in conjunction with a fluid handling device or system. In embodiments, a sample handling device may comprise a gantry, or may be configured to operate in conjunction with a gantry. In embodiments, a fluid handling device may comprise, or be configured to operate in conjunction with, a gantry.

In embodiments, a device as disclosed herein may include a light source, and may include optical elements (e.g., one or more of a lens, a grating, an aperture, a filter, a polarizer, or other element or elements) configured to provide light for illuminating a sample. In embodiments, light source for illuminating a sample may be emitted from a light source and then pass directly to the sample. In embodiments, a light source configured for illuminating a sample may be emitted from a light source and may then pass to, onto, through, or by, a grating, a mirror, a lens, a filter, a pin-hole, or other optical element or device, prior to passing to the sample. In embodiments, light for illuminating a sample may be emitted from a light source and may be split into two or more light paths; said two or more light paths may be directed along the same, or along similar, or along different, paths. In embodiments, one or more of said two or more light paths may be directed to a sample.

In embodiments, a device as disclosed herein may comprise a mirror or other reflective surface. It will be understood that a mirror may be configured to reflect some, or may be configured to reflect substantially all, of the light impinging on that mirror from a light source, or a mirror, or a lens, or a grating, or other source.

In embodiments, a device as disclosed herein may comprise a diffractive element, e.g., diffraction grating, diffractive lens, diffuser, beam splitter, corrective lens, or other surface or element configured to diffract light. In embodiments, a device as disclosed herein may comprise a pin-hole, or slit, or plurality of pin-holes, a slit or slits, or other optical elements configured to provide diffraction or interference with light. Diffraction (and interference) may affect transmitted, or reflected light (and, where reflected light interacts with incident light, may affect incident light as well). It will be understood that an optical element comprising a diffractive element or diffractive surface may be configured to diffract some, or substantially all, of the light impinging on, passing through, or reflected from that optical element from a light source, or a, or a lens, or a grating, or other source. It will be understood that a light source may be configured may direct some, or substantially all, of its emitted light onto a sample, or onto a surface, or onto or through a lens, or a grating, or a slit, or a hole, or other object, optical element, or location.

In embodiments, the device may be an optical measurement device. In embodiments, the device may be an optical imaging device. In embodiments, the device may be configured to measure or detect optical intensity. In embodiments, the device may be configured to measure or detect absorbance of light. In embodiments, the device may be configured to detect or measure spectral information from light passing through, or reflected from, or diffracted by, or emitted from, a sample or portion thereof. In embodiments, the device may be configured to detect or measure light scattering information from light passing through, or reflected from, or diffracted by, or emitted from, a sample or portion thereof. In embodiments, the device may be configured to detect or measure polarization information from light passing through, or reflected from, or diffracted by, or emitted from, a sample or portion thereof. In embodiments, the device may be configured to detect or measure other optical information from light passing through, or reflected from, or diffracted by, or emitted from, a sample or portion thereof.

In embodiments, a device configured for operation in may comprise a light source, and may include a light source lens (or lenses) configured to direct light from said light source onto a first optical element mounted on a rotatable mount. Light passing to and through a first lens (or first set of lenses) may be directed onto, and in embodiments may be directed through, a sample (e.g., a sample held in or by a sample holder). A mirror mounted on a rotatable mount may be used. Such light may be reflected to a reflective surface of a second optical element and thereby reflected and directed to a photodetector for observation, measurement, or analysis.

In embodiments, a light source of a unified detection device may comprise a light source selected from an incandescent lamp, a flash lamp, a laser, a light-emitting diode, and an arc light. In embodiments, a unified detection device as disclosed herein may further comprise one or more of a grating, an aperture, a filter, and a polarizer. In embodiments, a photodetector of a unified detection device as disclosed herein may comprise an optical component selected from a photodiode, a photomultiplier, a charge-coupled device (CCD), a spectrophotometer, a camera, and a microscope.

The devices, systems, and methods disclosed herein provide multiple optical capabilities in a single device or system. Devices disclosed herein are capable of performing spectroscopic, fluorescence, and luminescence observations, measurements and analyses; systems including these devices are also capable of performing all such optical observations, measurements and analyses. Provision of such multiple capabilities in a single device or in a single system may eliminate the need to move or load a sample in multiple devices when subjecting a sample to multiple analyses; thus, devices, systems and methods disclosed herein may provide greater accuracy, precision, and speed of sample analysis. Eliminating the need to load a sample on multiple devices for multiple analyses may reduce degradation of a sample where the time to perform multiple analyses is reduced as compared to prior devices, systems, or methods requiring use of multiple devices or systems. Provision of such multiple capabilities in a single device or in a single system may thus simplify and streamline the observation, measurement, and analysis of samples. Provision of such multiple capabilities in a single device or in a single system may reduce the time required, and may reduce the cost of, the observation, measurement, and analysis of samples. Providing such multiple capabilities in a single device or in a single system may simplify the design and operation of machines and systems for observing, measuring, and analyzing samples. Thus, devices, systems and methods disclosed herein provide greater ease, accuracy, precision, and speed of sample analysis while reducing the complexity and cost of such analyses. Accordingly, the devices, systems, and methods disclosed herein provide advantages over prior devices, systems, and methods.

In one non-limiting example, a sample verification device is provided for use with a sample container containing a sample. The device comprises at least one image capture device; a sample container support; and at least one communication module, wherein said at least one image capture device is aligned to collect visual information about at least one characteristic of the sample and at least one sample identifier associated with the sample whereby at least a portion of the information is transmitted by the communication module where said information is processed to alert a user if the sample fails to meet one or more sample collection criteria.

It should be understood that one or more embodiments herein may be modified to have one or more of the following features. For example, the sample verification device may include a multi-axis image capture system comprising the at least one image capture device along a first axis and at least another image capture device along a second axis. Optionally, a multi-axis information capture system is provided comprising the at least one image capture device along a first axis and at least another data reader along a second axis. Optionally, a multi-angle information capture system comprising using the at least one image capture device and optical element to simultaneously image more than surface of the sample container. Optionally, a light controlled housing for containing at least a portion of the sample and at least a portion of the at least one image capture device. Optionally, the light controlled housing comprises a portion movable from a closed position to an open position to allow for loading of the sample container into the sample verification device. Optionally, a region of interest of the at least one image capture devices comprises visualizing portions of at least two sample vessels. Optionally, a region of interest of the at least one image capture devices simultaneous images a portion of the sample and the visual identifier on the sample vessel. Optionally, a region of interest of the at least one image capture devices simultaneous images a portion of the sample and a visual identifier on the sample vessel. Optionally, other embodiments may use an information storage unit using a different technology such as but not limited to RFID to provide identifier information. Identification elements, devices, or systems for identifying and tracking samples may include but are not limited to bar codes and bar code readers; quick response (QR) code elements and readers; near field communication (NFC) elements and readers; radiofrequency identification (RFID) elements and readers; and other such identification elements and readers currently known or to be developed in the future. In such embodiment(s), an appropriate detector or detectors can be used for obtaining the desired information about the sample or sample vessel.

In another non-limiting example, a method of performing sample verification is provided, the method comprising capturing information about at least one characteristic of the sample; capturing at least one sample identifier associated with the sample; keeping the subject at the sample collection facility until sample verification is completed; and communicating an alert to a user if the sample fails to meet at least one sample collection criteria, whereby a remedial action is taken before the subject departs from the sample collection facility.

It should be understood that one or more embodiments herein may be modified to have one or more of the following features. For example, the method may further comprise placing the sample into a light-controlled imaging location. Optionally, the method of capturing comprises multi-axial imaging. Optionally, the method of comprises multi-angle imaging. Optionally, the method of capturing comprises multi-angle imaging using a single capture device. The single imager may use an optical element such as a dichroic or mirror to obtain imagery of a portion of the sample not directly in the linear line of sight of the image capture device. The method of data and sample capture may be simultaneous or from same collection event. Sample verification may involve characterizing two or more characteristics of the sample and this analysis may occur onboard the sample collection device or on a device or processor external to the verification device. Optionally, a system may be provided with a sample integrity data logger or other longitudinal tracking capability to establish a record of the samples being collected based on a certain selection criteria such as but not limited to the technician performing the collection, patient information, volume of sample being collected, time of day the sample is being collected, geography of the collection, or other external data that may be relevant to analysis of the collection event. Optionally, sample integrity can be determined based on at least one pre-selected set of sample characteristics. Some embodiments may also include a temperature sensor to determine by direct contact, by laser, or other indirect method the current temperature of the sample vessel or the sample therein. Optionally, some embodiments may substitute one or more of the image capture devices with a smart phone that has a camera mounted in a slot or adapter of the sample verification device. Optionally, this additional camera may be additive to the cameras in the sample verification device. In such an embodiment, the sample verification device may be in wireless or wired communication with the smart phone camera to provide coordination of the data capture. The smart phone camera may capture an image of a different angle of the sample. Optionally, the smart phone camera may be mounted in a slot that provides a different angled view. Optionally, the smart phone is mounted external to the sample verification device but is in optical communication with an optical train that provides the smartphone camera with a view at a desired region of interest. A flash or other light source from may also be used with the sample verification device. Optionally, some embodiments of the sample verification device do not provide any data capture, machine reader, or other imaging sensor built into the device, but instead, functions more as a jig to position a smart phone or other mobile computing device with at least one camera to capture information about the sample. Such an embodiment may function to consistently position the sample and/or provide a controlled light environment for image capture. Optionally, some embodiments may include only one data capture or non-image capturing data reader and relies on the smart phone for other capture capabilities. Optionally, some embodiments may use optical elements such as mirrors, fiberoptics, light guides, or the like to utilize both front and back facing cameras on a smart phone to provide multiple images of the sample vessel. In some embodiments, a barcode or other graphic data code is place only on a side of sample that will also be imaged for sample verification so that a single can do image capture and ID capture; the barcode or other graphic data code can be in the region of interest for sample verification or at a location away from the region of interest but still capturable in the field of view by a single camera so that the ID or other information for the sample can be recorded. Optionally, the condition of the sample in the sample vessel can be ascertained without other further analysis of the sample. Optionally, the condition of the sample in the sample vessel can be ascertained without chemical analysis of the sample. Optionally, the condition of the sample in the sample vessel can be ascertained without analyte testing of the sample. Optionally, the condition of the sample in the sample vessel can be ascertained without removal of the sample from the sample vessel.

In yet another embodiment described herein, a method is provided of performing two or more laboratory tests with a small volume bodily fluid sample from a single subject, the method comprising: obtaining at a sample collection site at least a first vessel containing a first portion of a sample and a second vessel containing a second portion of the sample, wherein the sample is a small volume bodily fluid sample collected from a single subject, and wherein the total volume of the sample collected from the single subject is no greater than 400 microliters; transporting the first vessel and the second vessel from the sample collection site to a sample receiving site; and performing at the sample receiving site one or more steps of a first laboratory test with at least a portion of the first portion of the sample and one or more steps of a second laboratory test with at least a portion of the second portion of the sample. Optionally, a sample verification step may occur prior to the transporting step. Optionally, the first portion of the sample and the second portion of the sample each comprise an anticoagulant. Optionally, the anticoagulant in the first portion of the sample differs from the anticoagulant in the second portion of the sample. Optionally, the anticoagulant in the first portion of the sample is EDTA and the anticoagulant in the second portion of the sample is heparin. Optionally, the sample collection site and sample receiving site are separated by at least 1 kilometer. Optionally, the first vessel and second vessel arrive at the sample receiving site no more than 12 hours after the bodily fluid sample was obtained from the subject. Optionally, the sample is obtained from the subject's digit, which has been punctured to release the sample from the subject. Optionally, the first portion of the sample is maintained in liquid form during the transporting of the first vessel from the sample collection site to the sample receiving site.

In yet another embodiment described herein, a method is provided for performing two or more laboratory tests with a small volume bodily fluid sample from a single subject, the method comprising: obtaining at a sample collection site at least a first vessel containing a first portion of a sample and a second vessel containing a second portion of the sample, wherein the sample is a small volume bodily fluid sample collected from a single subject, and wherein the total volume of the sample collected from the single subject is no greater than 400 microliters; transporting the first vessel and the second vessel from the sample collection site to a sample receiving site; removing at the sample receiving site from the first vessel a first vessel original sample, wherein the first vessel original sample is at least a portion of the first portion of the sample; generating a first vessel dilution sample from the first vessel original sample, wherein the first vessel dilution sample: i) is diluted at least 3-fold as compared to the first vessel original sample, and ii) has a total volume of no more than 1000 microliters, and performing at the sample receiving site one or more steps of a first laboratory test with at least a portion of the first vessel dilution sample and one or more steps of a second laboratory test with at least a portion of the second portion of the sample. Optionally, a sample verification step may occur prior to the transporting step. Optionally, the first portion of the sample and the second portion of the sample each comprise an anticoagulant. Optionally, the anticoagulant in the first portion of the sample differs from the anticoagulant in the second portion of the sample. Optionally, the anticoagulant in the first portion of the sample is EDTA and the anticoagulant in the second portion of the sample is heparin. Optionally, the sample collection site and sample receiving site are separated by at least 1 kilometer. Optionally, the first vessel and second vessel arrive at the sample receiving site no more than 12 hours after the bodily fluid sample was obtained from the subject. Optionally, the sample is obtained from the subject's digit, which has been punctured to release the sample from the subject. Optionally, the first portion of the sample is maintained in liquid form during the transporting of the first vessel from the sample collection site to the sample receiving site.

Optionally, a method is provided comprising at least one technical feature from any of the prior disclosed features. Optionally, a method is provided comprising at least any two technical features from any of the prior disclosed features. Optionally, a device comprising at least one technical feature from any of the prior disclosed features. Optionally, device comprising at least any two technical features from any of the prior disclosed features. Optionally, a system comprising at least one technical feature from any of the prior disclosed features. Optionally, a system comprising at least any two technical features from any of the prior disclosed features.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
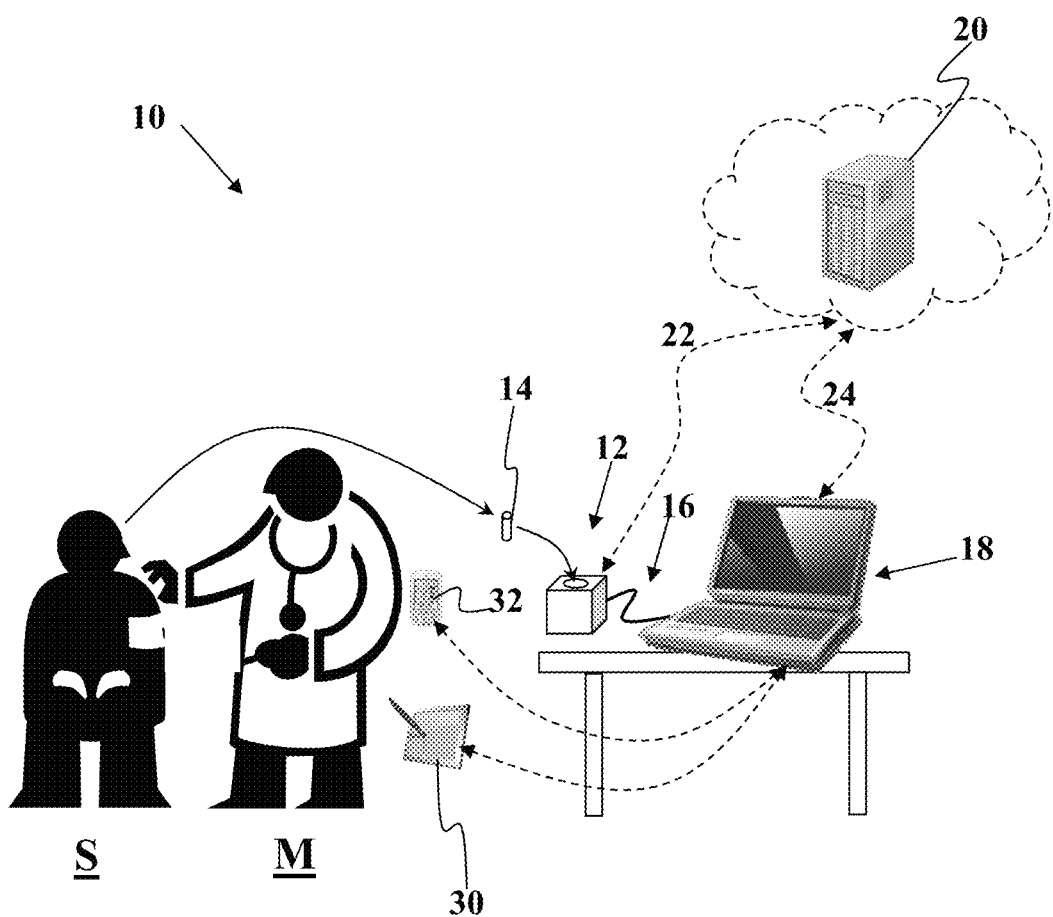
FIG. 1 illustrates one embodiment of a system including one embodiment of a device as disclosed herein.

Description and disclosure which may aid in understanding the full extent and advantages of the devices, systems, and methods disclosed herein may be found, for example, in PCT Application Ser. No. PCT/US13/58627, U.S. patent application Ser. No. 13/769,820 (filed Feb. 18, 2013), Ser. No. 14/446,080 (filed Jul. 29, 2014), 62/210,968, and 62/237,527, the disclosures of which are all hereby incorporated by reference in their entirety for all purposes. The publications discussed or cited herein are provided solely for their disclosure prior to the filing date of the present application. Nothing herein is to be construed as an admission that the presently disclosed systems, devices, and methods are not entitled to antedate such publication by virtue of prior invention.

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2014-2015 Thermos, Inc.

In this specification and in the claims which follow, reference will be made to a number of terms which shall be defined to have the following meanings:

It is to be understood that both the foregoing general description and the following detailed description are exemplary and explanatory only and are not restrictive, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like.

As used in the description herein and throughout the claims that follow, the meaning of "or" includes "and/or" (i.e., "or" includes both the conjunctive and disjunctive) unless explicitly stated otherwise, or unless the context expressly dictates otherwise.

As used in the description herein and throughout the claims that follow, the meaning of "in" includes "in" and "on" unless the context clearly dictates otherwise.

References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a urine sample, a tissue sample (e.g., a biopsy sample or a tissue slice), or other biological sample, however obtained or prepared. A blood sample may be, for example, obtained from a finger-stick, or from venipuncture, or an arterial blood sample, and may be whole blood, serum, plasma, or other blood sample. Further examples of samples include, without limitation, a water sample, a soil sample, a food sample, an air sample; or other sample (e.g., a stool sample, a throat swab, a nasal swab or nasopharyngeal wash, a sample of saliva, urine, tears, gastric fluid, spinal fluid, mucus, sweat, earwax, oil, glandular secretion, cerebral spinal fluid, tissue, semen, cervical fluid, vaginal fluid, synovial fluid, breath, hair, finger nails, skin, biopsy, placental fluid, amniotic fluid, cord blood, lymphatic fluids, cavity fluids, sputum, mucus, pus, microbiota, meconium, breast milk or other secretion or excretion).

Thus, as used herein, a "sample" includes a portion of a blood, urine, or other biological sample, may be of any suitable size or volume, and is preferably of small size or volume. In some embodiments of the systems, assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, an "optical detector" detects electromagnetic radiation (e.g., light). An optical detector may detect an image or be used with an image, or may detect light intensity irrespective of an image, or both. An optical detector may detect, or measure, light intensity. Some optical detectors may be sensitive to, or restricted to, detecting or measuring a particular wavelength or range of wavelengths. For example, optical detectors may include, for example, photodiodes (including, e.g., avalanche photodiodes), photomultipliers, charge-coupled devices (CCDs), spectrophotometers, cameras, microscopes, and other devices (e.g., phototransistors, phototubes, photoresistors, photovoltaics, and other light-sensitive components, elements, and devices, embodying any suitable technology (including, e.g., complementary metal oxide semiconductor (CMOS), N-type metal oxide semiconductor (NMOS), thin-film transistor (TFT), and other technologies)) which detect light or measure light intensity (of a single wavelength, of multiple wavelengths, or of a range, or ranges, of wavelengths of light), form an image, or both.

As used herein, the term "microscopy" refers to optical methods which involve imaging a sample, and which typically involve magnification, enlargement, or other techniques in order to provide a magnified image of a sample or portion of a sample. Microscopy may involve one or more of fluorescence microscopy, dark field microscopy, bright field microscopy, interference contrast microscopy, phase contrast microscopy, and other microscopy methods to image, observe, or measure one or more portions of a sample or attributes of a sample or portion thereof. Such methods may, e.g., provide morphometric information regarding cells, particles, or other portions or constituents of a sample. Such information may be measured quantitatively. In some embodiments, for quantitative microscopy, a sample is analyzed by two or more of quantitative fluorescence microscopy, quantitative dark field microscopy, quantitative bright field microscopy, and quantitative phase contrast microscopy. Quantitative microscopy may include use of image analysis techniques and/or statistical learning and classification methods to process images obtained by microscopy.

A sample to be analyzed, e.g., by optical or imaging means, may be held in a sample holder for analysis. For example, a cuvette may serve as such a sample holder. Other sample holding devices may also be used in place of or in combination with a cuvette. For example, a microscope slide may serve as a sample holder; a tube may serve as a sample holder; a clamp may serve as a sample holder; a receptacle may serve as a sample holder; a surface may serve as a sample holder; or other object, implement, or device may serve to hold a sample, or portion thereof, for optical observation, measurement, or analysis.

Similarly, and without limitation, other elements may be mounted on rotatable or otherwise movable mounts, in order that, for example, a lens, or filter, or prism, slit, pin-hole, or other optical element can be moved in order to adjust the placement of that element in the light path, or to remove the element from the light path. For example, such movement may include rotation (e.g., around an axle or other mount), transverse motion (e.g., along a direction substantially perpendicular to a light path), longitudinal motion (e.g., along a direction substantially parallel to a light path), other lateral motion, or a combination thereof. Such movement may be useful to make minor adjustments or corrections in position or orientation of the optical element; may be useful to make substantial changes in the position or orientation of the optical element (e.g., movement of the optical element into, or out of, an optical path); or combinations thereof.

An optical detector such as but not limited to a photodiode, a CCD, or other optical detector may be configured for use in both a digital (e.g., counting) mode and an analog mode, and may be configured to switch between these modes as needed for a particular application or a particular observation, measurement, or analysis.

Further elements which may be included in devices and systems disclosed herein, or which may be used in conjunction with devices and systems disclosed herein, include, for example, a fluid handling device or system that is configured to transport a sample, a sample holder, or other object or container to the measuring area. Further elements which may be included in devices and systems disclosed herein, or which may be used in conjunction with devices and systems disclosed herein, include, for example, a pipette and gantry system that prepares the samples, or transports them to the measuring area. Devices and systems disclosed herein may include, or may be used in conjunction with, identification elements, devices, or systems for identifying and tracking samples (e.g., bar codes and bar code readers; quick response (QR) code elements and readers; near field communication (NFC) elements and readers; radiofrequency identification (RFID) elements and readers; and other such identification elements and readers).

In embodiments, a mirror, lens, optical element, or other component of a unified detection device or system may be mounted so as to be rotatable (or otherwise adjustable). Such rotatable or otherwise adjustable mounting configurations may utilize a rotor; an axle; a pivot; a hinge; a bearing; a belt; a slide or way; a cam; or other movable (including slidable) part. Such rotatable or otherwise adjustable mounting configurations may include a motor (including a stepping motor); a screw or other threaded component; a piston; a piezoelectric actuator or positioner; a pneumatic or hydraulic positioner or drive; or other motive element. Such rotatable or otherwise adjustable mounting configurations may include tubing, wiring, springs, tensioners, gaskets, attachment elements such as clamps, bolts, glue, fasteners, friction plates, supports, and other mechanical and structural elements.

Referring now to FIG. 1, at least one embodiment of system 10 having a sample verification device 12 will now be described. As seen in FIG. 1, a sample 14 is collected from the subject S by a medical staff person M. It should be understood that other techniques for sample acquisition are not excluded. In this non-limiting example, the sample 14 can be inserted into or otherwise operably engaged with or positioned to operate with the sample verification device 12. FIG. 1 shows that the sample verification can be coupled by a wired connection 16 or other communication channel with a computer 18. Optionally, wireless, bluetooth, RF, NFC, 3G, 4G, 4GLTE, WiMax, other current or future communication protocol, or other non-wired communication link can also be used. Although FIG. 1 shows the sample verification device 12 and the computer 18 as separate device, it should be understood some embodiments may combine both into one hardware unit, one functional unit, or the like. Some embodiments may include at least one processor in the sample verification device 12 to provide some capability to assess the sample, image of the sample, and/or data from the sample. Some embodiments may include one or more data capture facilities in the computer to capture information about one or more characteristics of the sample(s).

In one non-limiting example, a system 10 may optionally include a remote computing resource 20, such as but not limited to a server or other external computing device, which may be operably in communication with the device 12 or computer 18 via communication channels 22 or 24 respectively, effective that information obtained by the imager pursuant to its observation, measurement or analysis of samples may be communicated to a user, an external device, a database, a network, or other device or system. A user, external device, network, or other device or system may monitor, or may provide oversight of, the verification device 12 or its operation via a communication device in the device or through the computer 18, via communication channels 22 or 24 respectively. In one non-limiting example, a communication device and a communication channel may be effective to provide instructions to, or to otherwise control the operation of the verification device 12. A communication device or a communication channel may be present, and may be used, in addition to, or in place of, a communication component or a communication channel which may be included in a sample verification device 12 as disclosed herein. In one non-limiting example, the verification device 12 can be viewed as a data capture device and the analysis of the data occurs off-board of the device 12, such as but not limited to being performed on an associated computer 18 or on a remote computing resource 20. In one non-limiting example, analysis of one or more characteristics of the sample or samples occurs on-board the verification device 12. Optionally, some embodiments may be a combination of the foregoing wherein a portion of the analysis occurs on the device 12 and a portion occurs off-board in an external device. Optionally, some embodiments may do substantially similar verification of the sample at verification device 12 and at an offsite computing device to reduce the risk that one of the devices is not performing as desired. In one non-limiting example, at least one portion of the verification occurs in a first time period and then a second verification occurs in at least a second time period. In one non-limiting example, the same verification is performed in at least the first and second time periods. Optionally, verification is different between at least two of the time periods. Some embodiments may perform same or different verification over three or more time periods.

If an anomaly is detected, information about this anomaly can be communicated to a user, medical professional, an external device, a database, a network, or other device, system, or personnel. In one non-limiting example shown in FIG. 1, an alert, information about the anomaly, or an indicator can be sent to a display on computer 18, on the device 12, or to peripheral devices such a mobile computer, tablet computer 30, or smart phone 32. It should be understood that the information may be conveyed in a visual, audio, tactile, touch, vibration, other sensory manner to a recipient, or single or multiple combinations of the foregoing. By way of non-limiting example, information being conveyed may be simple or basic, such as but not limited to indicating an issue with the sample without being specific as to the issue. Optionally, some may be qualitative instead of quantitative in the reporting. Optionally, some embodiments can be configured to provide at least some information about what characteristic of the sample triggered the alert. By way of non-limiting example, the alert may be sent by short message service (SMS), text message, email, voicemail, video call, or other message sending protocol, including those that may be developed in the future. Optionally, some embodiments can be configured to provide at least some information about what action to take next, be it corrective action or follow-up action to verify the fault triggering condition. Optionally, some embodiments may be operated in a manual review mode where each sample image is Based on the sample characteristic(s) captured by the sample verification device 12, the medical professional M or other personnel can take action to rectify the issue. In one non-limiting example, this involve collecting more sample from the subject S before the subject S leaves the sample collection facility. This may involve repeating the collection process, collecting only an additional portion desired to address any deficiency from the previous collection. Optionally, other embodiments may have still further options related addressing sample verification, such as but not limited user verification of the fault condition or further processing of the sample so that it can be deemed acceptable without having to obtain further sample. Although many of the examples herein describe the sample as a blood sample, it should be understood that the sample from the subject is not limited to such blood samples and in some implementations, may be urine or other types of samples. In one non-limiting example, the sample verification device 12 can be used to determine sample volumes and other basic information about the sample before the sample is further processed.

Figure 2:
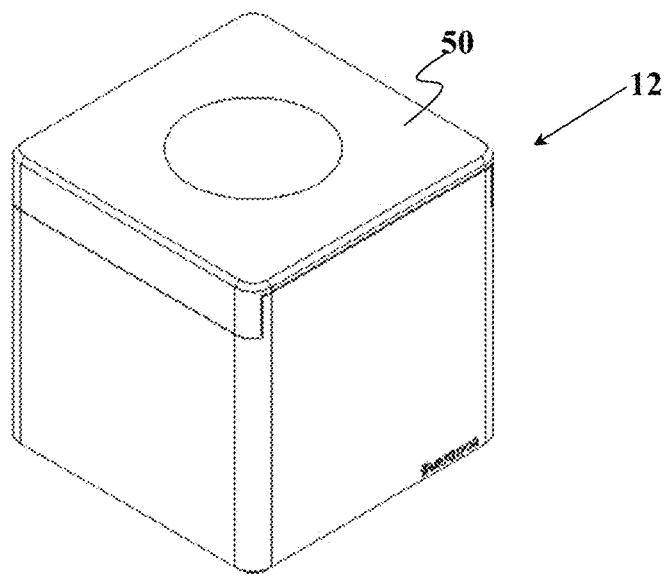
FIGS. 2 to 4 show various embodiments of a device as disclosed herein.
Figure 4:
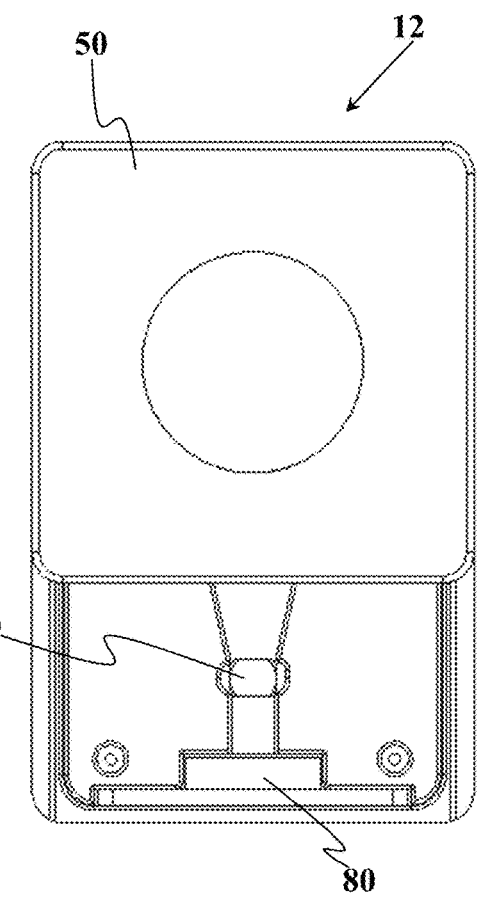
Figure 3:
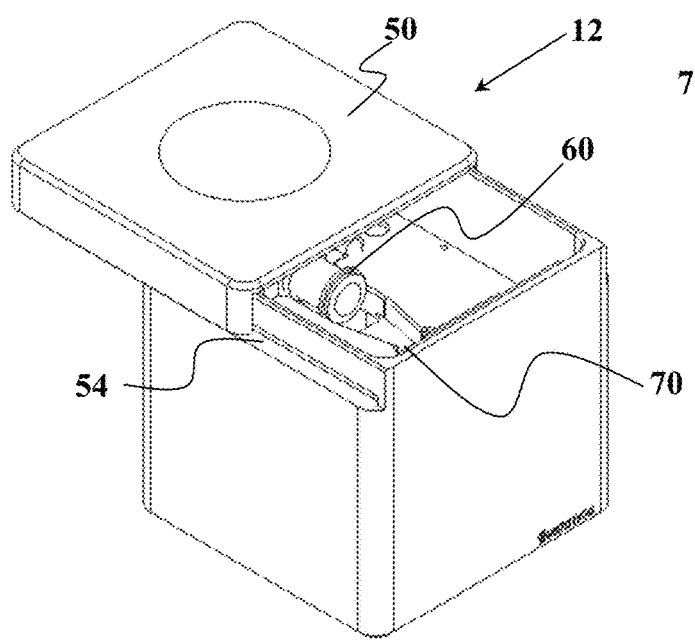

Referring now to FIGS. 2 to 4, one embodiment of a sample verification device 12 will be described. FIG. 2 shows an embodiment of the sample verification device 12 wherein the lid 50 is in a closed position. In some embodiments, blocking ambient light can be useful to reduce variance in images or other data being collected about the sample. In this manner, the conditions of the imaging or other data collection can be more consistent from sample to sample. Although the lid 50 in the close position minimizes the amount of ambient light entering the device 12, it should be understood that some alternative embodiments may not have a lid that moves to fully close the interior of the device 12 from exterior light and such embodiments are not excluded. Optionally, in such embodiments, correction by way of software or other techniques may be used to reduce variability between images.

FIG. 3 shows another view of one embodiment of a sample verification device 12. In FIG. 3, the lid 50 is in an open position which allows for at least some internal components to be visualized in FIG. 3. In this non-limiting example, the lid 50 is movable in a slidable manner along a rail 54. Some embodiments may include a sensor to detect if the lid 50 is in the open or closed position. Optionally, some embodiments may place the sample container directly into an open slot a sample verification device that does not have a lid. FIG. 3 also shows that in the present embodiment, there is at least one imaging device 60 in the sample verification device 12 for characterizing one or more samples that may be in the device 12. Although FIG. 3 shows that the lid 50 is sized to be essentially an entire side of the sample verification device, some embodiments may use a smaller opening or cover that reveals only a certain area sized to allow for insertion and removal of a sample to be verified.

FIG. 4 shows a top-down view of one embodiment of the sample verification device 12 with the lid 50 in the open position. FIG. 4 shows a receiving location 70 in the sample verification device 12 where the sample(s) to be imaged may be placed. Although this embodiment shows the location 70 as having a specific shape conforming to the outline of the sample vessel, it should be understood that other embodiments may configure the receiving location 70 without having surfaces at the location 70 that conform to the shape of the sample vessel. Some embodiments may have a location 70 which a top-down shape such as but not limited to square, rectangular, circular, oval, or the like. Some embodiments may have an adapter with an outer perimeter shape that confirms to the shape presented at location 70, but have an inner perimeter shape that is shaped to conform to that of the sample vessel(s). It should also be understood that some embodiments may provide a light source, light conduit, or other illumination source or guide 80 that can be positioned to light the sample placed at location 70. An optical configuration in which the light source and the light detector are on opposite sides of an illuminated sample is termed a "backlit" configuration, in which the light source is configured to backlight the sample. An optical configuration in which the light source and the light detector are on the same side of an illuminated sample is termed a "frontlit" configuration, in which the light source is configured to frontlight the sample. Although in this non-limiting example the illumination source or light guide 80 is positioned to backlight the sample, it should be understood that other embodiment may use both backlighting and frontlighting. Optionally, some embodiments may only use frontlighting. Others may use one or more lighting source(s) at one or more off-angle positions, along with or in place of any backlight or frontlight. It should also be understood that the type of light used for illumination may also be pre-selected to have certain wavelength ranges and/or color temperature (as measured in Kelvin or other rating). Some embodiments may use fiberoptics or other optical elements to guide light to the desired location. Some embodiments may use edge lighting techniques to illuminate the desire area(s). Optionally, others may place the light source directly at or adjacent the desired location. Optionally, some embodiments may use one or more light sources with a color rendition index rate of at least 90. Optionally, some embodiments may use one or more light sources with a color rendition index rate of at least 92. Optionally, some embodiments may use one or more light sources with a color rendition index rate of at least 95.

Figure 5:
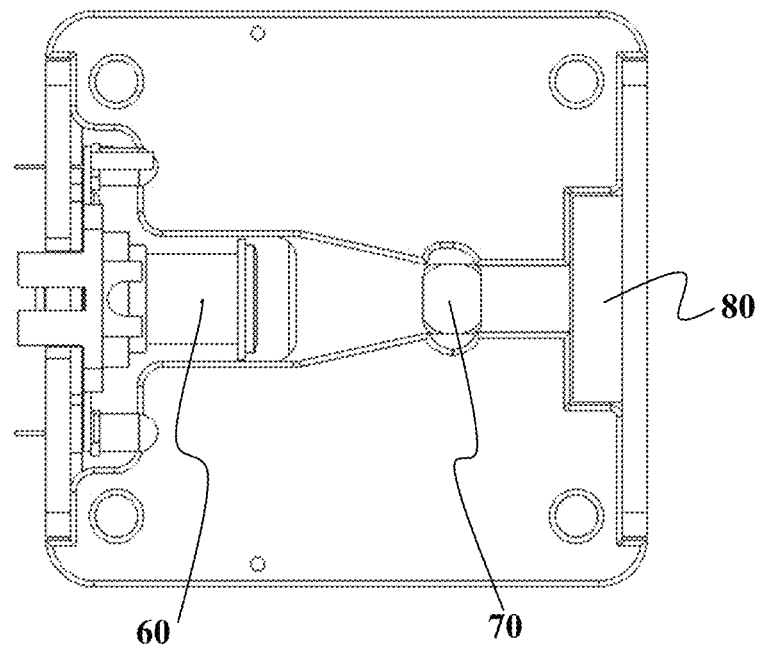
FIGS. 5 and 6 show top-down and bottom-up views of at least one embodiment of the internal components of a device as disclosed herein.
Figure 6:
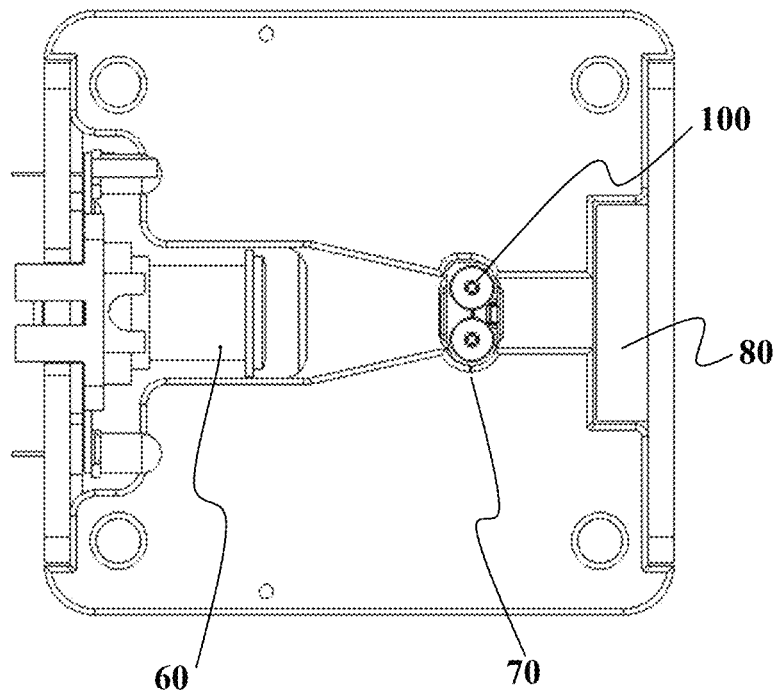

FIGS. 5 and 6 show top-down views of internal components of one embodiment of the sample verification device 12. FIG. 6 shows a container 100 having one or more sample vessels therein positioned at location 70 for sample verification. The verification may be by way of imaging through use of at least one imaging device 60. Although a camera may be used as the imaging device 60, it should be understood that other image capture, image data, or data acquisition device that may be developed in the future may be used or adapted for use as the imaging device 60.

Figure 7:
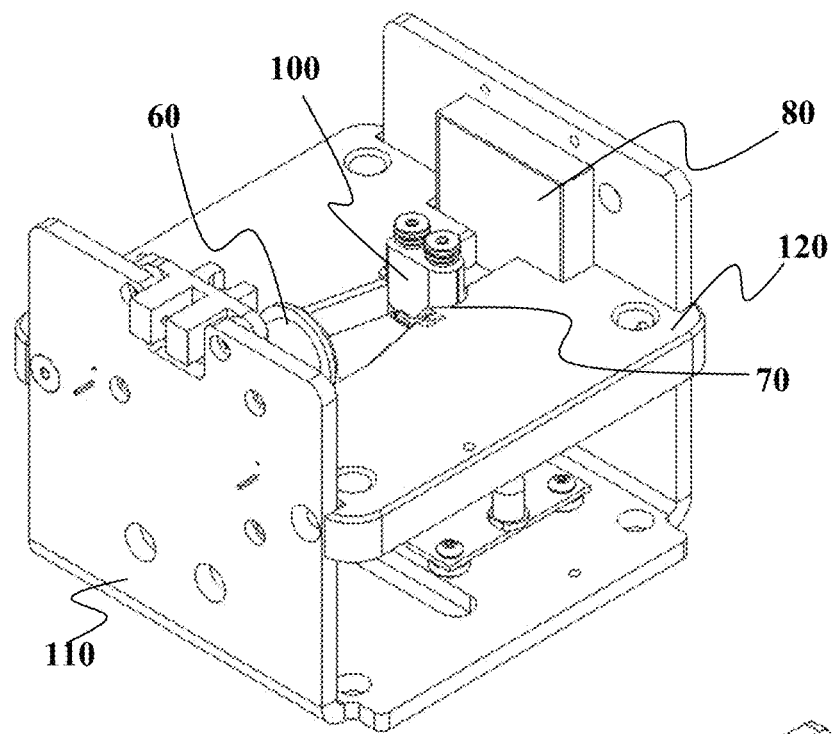
FIGS. 7 and 8 show perspective views of at least one embodiment of the internal components of a device as disclosed herein.
Figure 8:
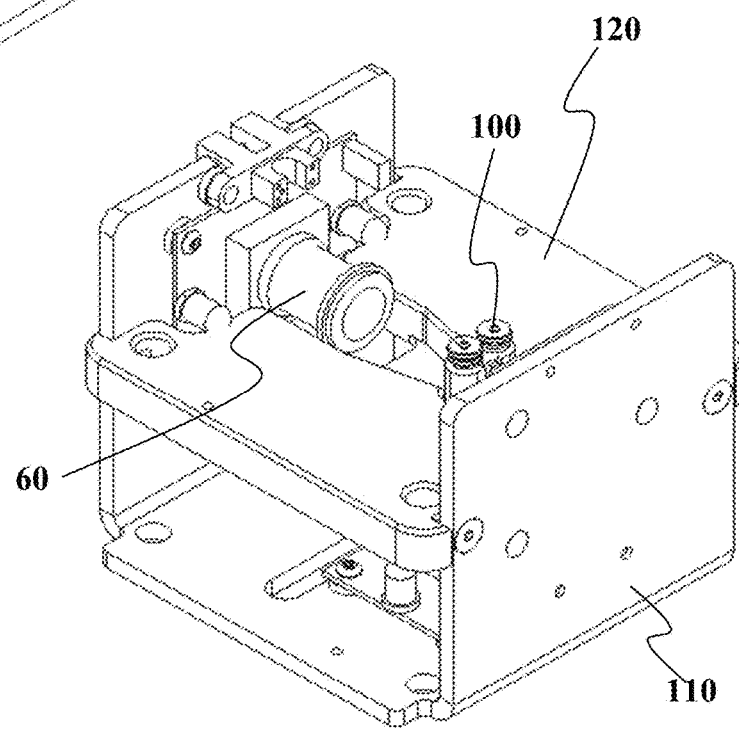

Referring now to FIGS. 7 and 8, various perspective views of internal components of the sample verification device 12. FIG. 7 shows a support 110 such as but not limited to internal frame on which at least some of the internal components are mounted. In at least one non-limiting example, there may be a platform portion 120 on which at least one imaging device 60 can be mounted in alignment with location 70 to facilitate sample verification. FIGS. 7 and 8 also show that a support structure such as but not limited to platform 120 can position the sample container 100 at a location so that a different portion of the sample container 100 can be imaged.

Figure 9:
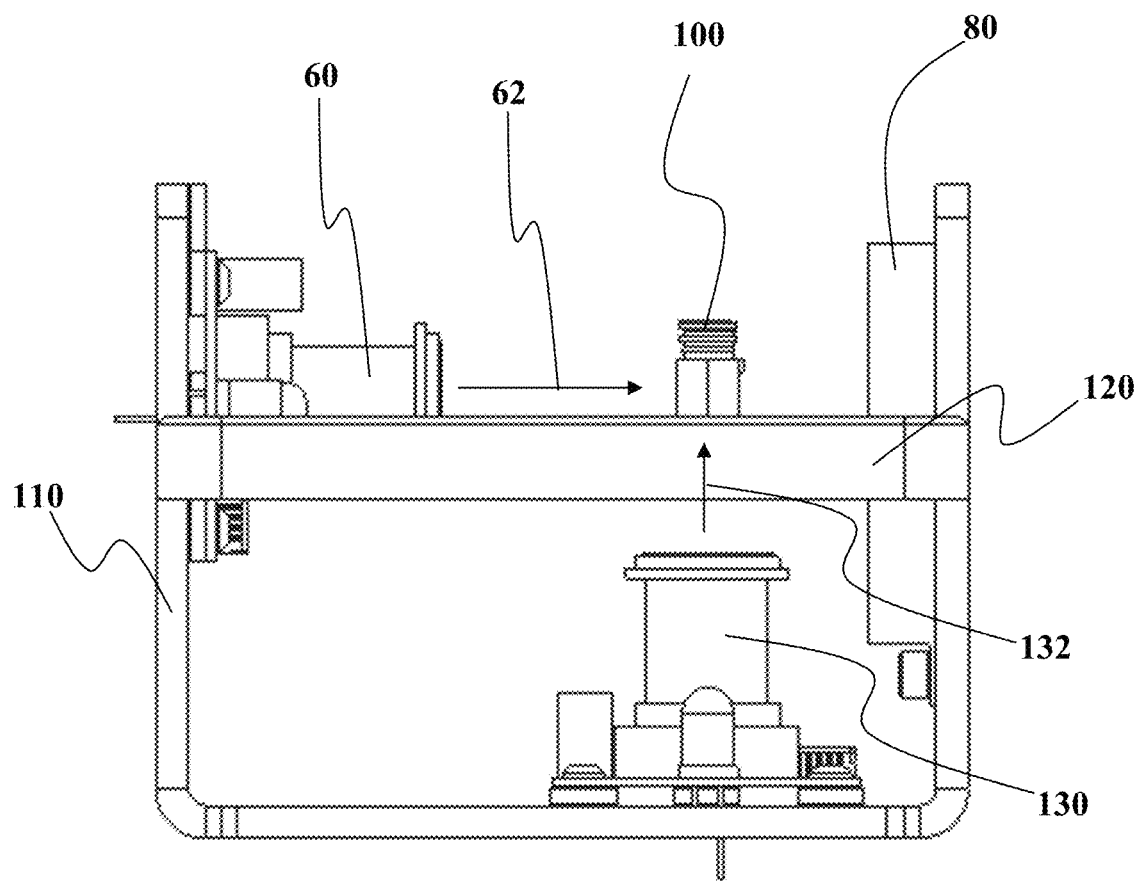
FIGS. 9 and 10 show side views of at least one embodiment of the internal components of a device as disclosed herein.

In one non-limiting example as seen in FIG. 9, at least another imaging device 130 can be positioned to view an underside surface of the sample container 100 as indicated by arrow 132. In this non-limiting example, the sample verification device 12 uses a multi-axis imaging system to capture image(s) along a first axis indicated by arrow 62 and also capture image(s) along a second axis indicated by arrow 132, simultaneously or sequentially. The non-limiting example of FIG. 9 uses two cameras for imaging devices 60 and 130. It should be understood that other embodiments may use a camera for one of the imaging devices and a non-imaging scanner such as but not limited barcode scanner for another of the data capture devices. Optionally, some embodiments may place the at least another imaging device 130 at another orientation in addition to or in place of the one shown to image a side surface, a top surface, a rear surface, or other surface of the sample vessel that may have a visual identifier. Optionally, an appropriately sized cut-out may be included in the platform 120 to allow for visualization of the target surface(s) which may have the detectable information. Optionally, other embodiments may use other data communication techniques such as RFID or other techniques as described elsewhere herein in addition to or in place of any visual identifying technique(s) used for the sample vessel(s). Information about the sample and/or sample vessel may be uploaded to a laboratory information system (LIS) or electronic medical records (EMR) system to record if there are any issues to correct for regarding the sample or if the results (should the sample be processed) be discarded if sample quality or other issued is noted as being below a threshold for reliable accurate results. By way of non-limiting example, one LIS system that may be used with the sample integrity information herein is described in U.S. application Ser. No. 14/341,745 filed Jul. 25, 2014 and fully incorporated herein by reference. Optionally, the device herein with the imaging device 60 may be coupled to or integrated with a sample processing device described in U.S. application Ser. No. 13/769,820 filed Feb. 18, 2013 and fully incorporated herein by reference. Optionally, the device herein with the imaging device 60 may be a stand-alone device for inspecting and/or performing formed component separation that has communication capability, such as but not limited to having hardware that allows the device to be internet-enabled through wired or wireless technology currently known or may be developed in the future.

Referring still to FIG. 9, it should be understood that in some embodiments, other cameras, optical sensors, and/or other detectors may be used in addition to imaging device 60 to identify qualities about the sample. Some may use other detector technologies (not merely optical) to interrogate the quality or integrity of the sample or the sample vessel. By way of non-limiting example, some embodiments may use at least one of a spectrophotometer, an absorbance detector, a turbidimeter, a color camera, an infrared detector, a non-visual wavelength detector, or other detector technology currently known or may be developed in the future. In embodiments, these other detectors may be stacked above, adjacent, or otherwise positioned to allow for an alignment that allows for interrogation of the sample or sample vessel. Some may opt for at least one servo, a motor, or actuator to cause relative motion of the sample vessel and the at least one detector(s). Although other techniques are not excluded, one embodiment may have an actuator rotate the sample vessel about an axis so that the detector may interrogate the sample without moving the detector. By way of non-limiting example, this may be achieved by a rotatable mount coupled to the platform, wherein a bearing, bushing, or other interface allows for the mount to rotate. The rotatable mount may include a cutout, wire framing, or other design to allow for visualization of the sample. Optionally, some embodiments may use transparent or other material for the sample vessel mount that allows for interrogation of the sample through the material. Optionally, another embodiment may have the detector mounted on a gantry and move the detector relative to a stationary sample vessel.

Figure 10:
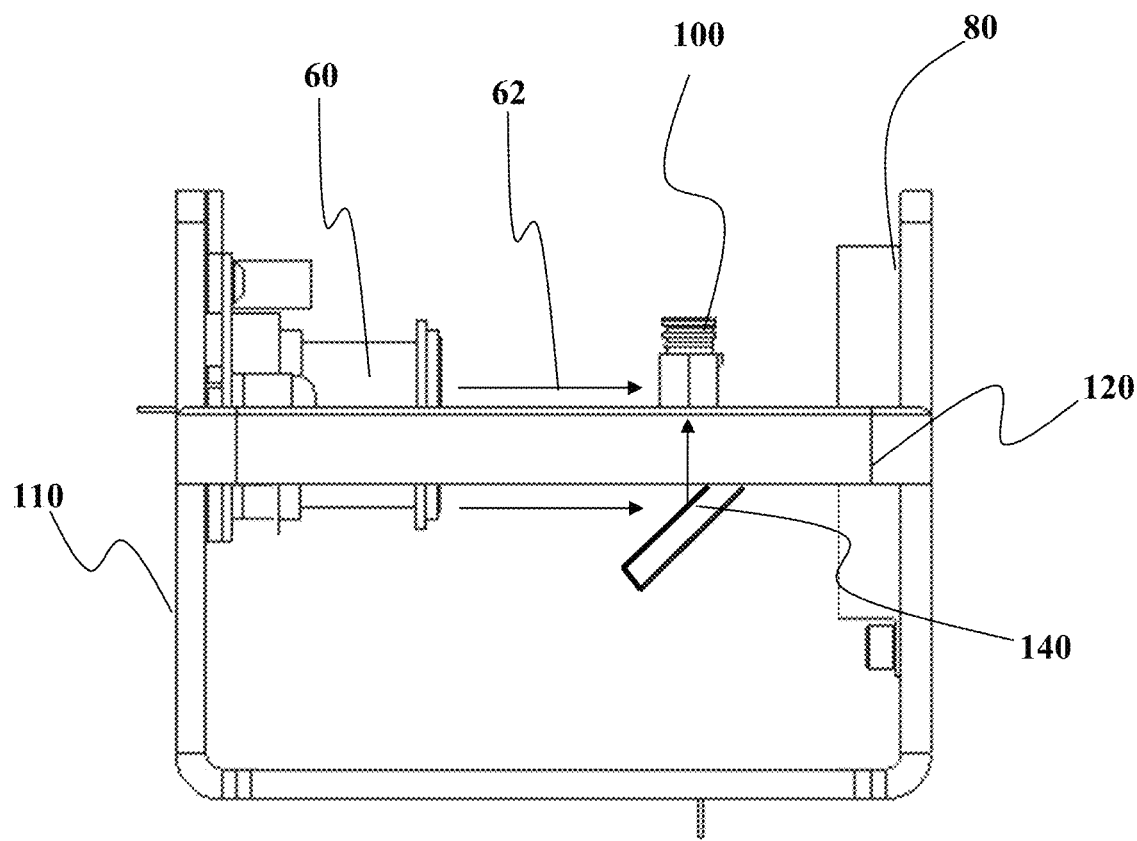

Optionally as seen in FIG. 10, some embodiments may have an optical element 140 such as but not limited to a mirror, dichroic, prism, or other optical element(s) positioned to allow at least a single camera to capture data from multiple surfaces of the target sample. By way of non-limiting example, one embodiment may have a mirror positioned below the location 70 but angled to allow the imaging device 60 to simultaneous view more than one surface of the sample container 100. Optionally, some embodiments may have a movable optical element that allows for control of when the other surface of the sample container 100 is visible to the image capture device.

Figure 11:
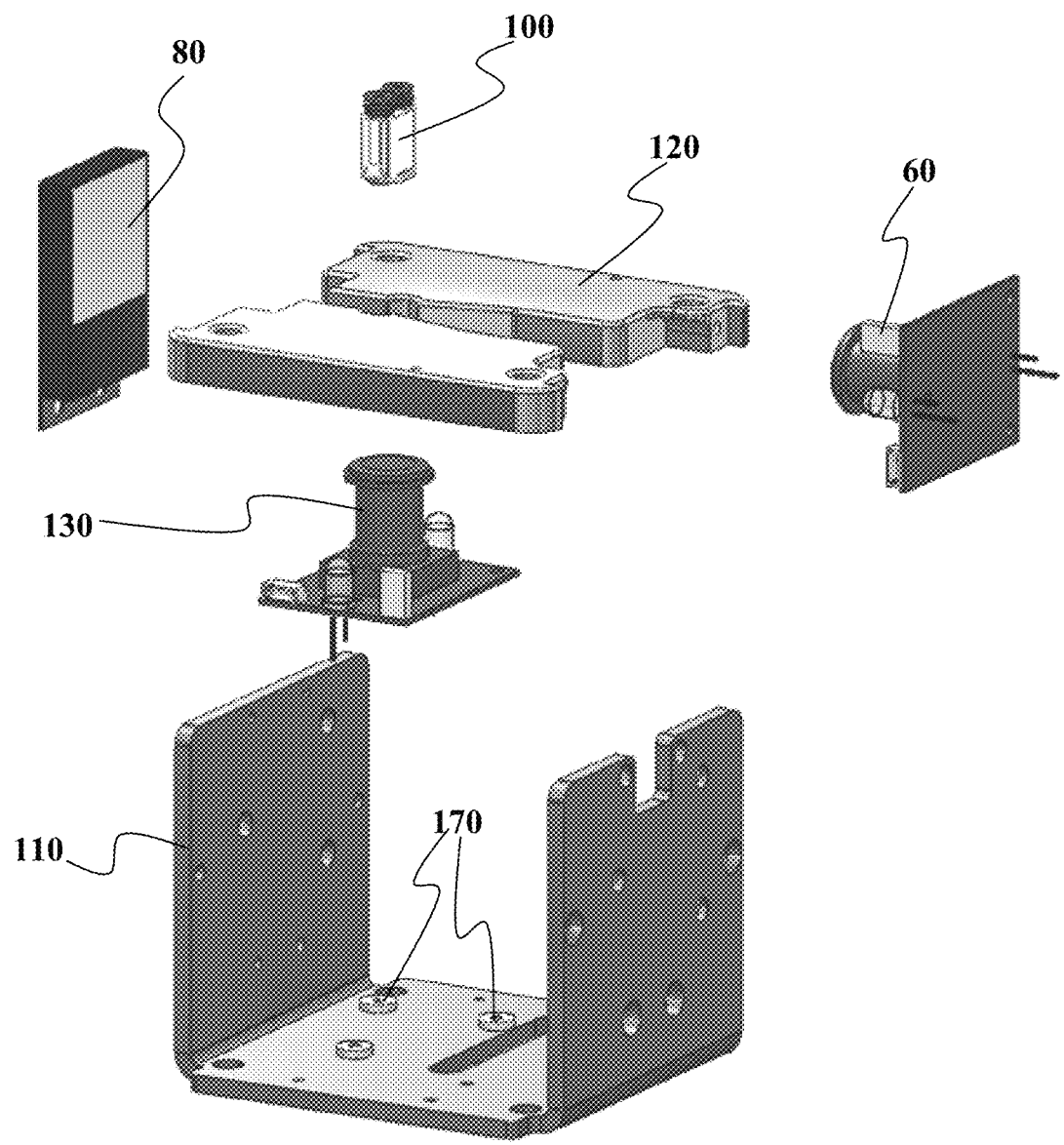
FIG. 11 shows an exploded view of at least one embodiment of the internal components of a device as disclosed herein.

Referring now to FIG. 11, an exploded perspective view is shown of various internal components of one embodiment of a sample verification device 12. As seen in FIG. 11, most of the components are mounted to the support 110. Some embodiments may include additional support elements such as compressible, semi-compressible, or solid spacers 170 to mount select components to the support 110.

Figure 12:
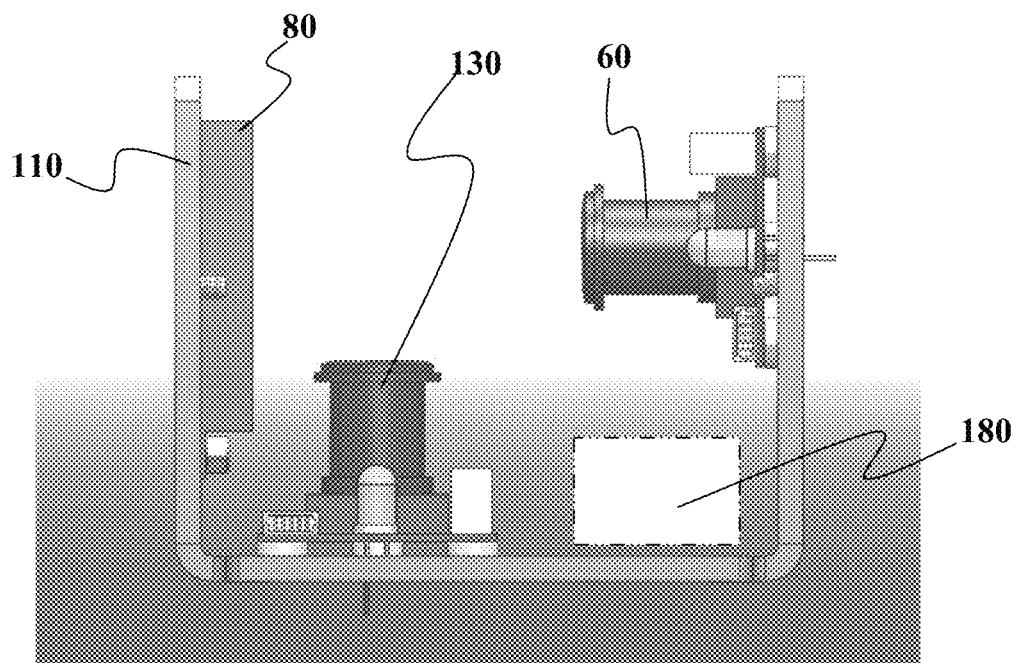
FIGS. 12 to 13 show various views of at least one embodiment of the internal components of a device as disclosed herein.
Figure 13:
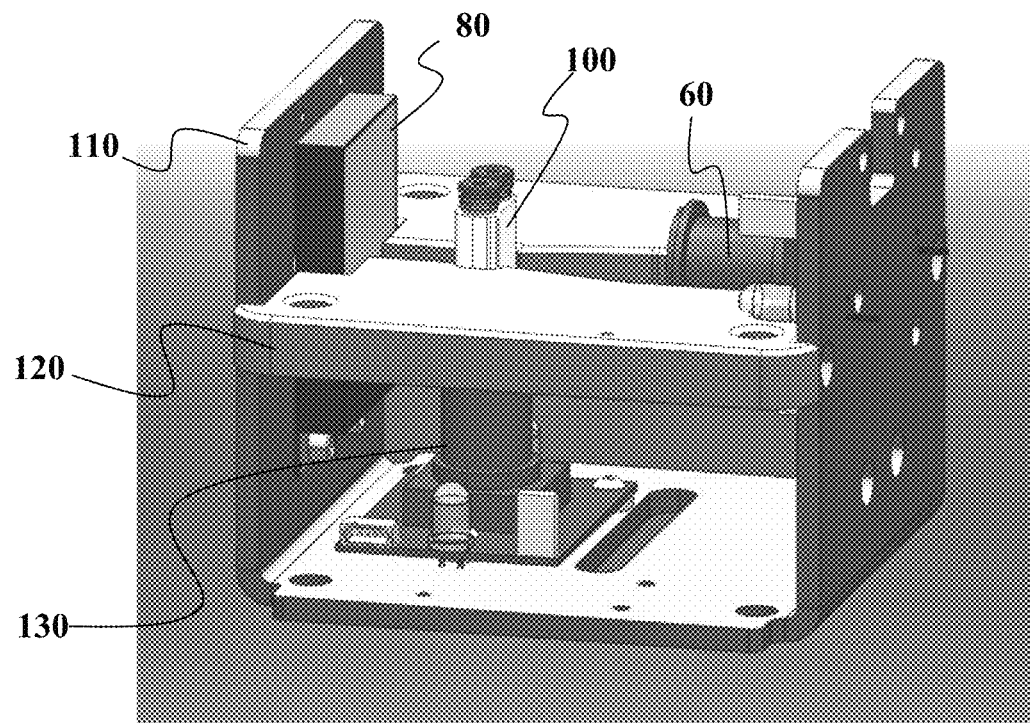

FIGS. 12 and 13 show additional views of various internal components of one embodiment of a sample verification device 12. Although most embodiments shown herein such as that of FIG. 12 may have two cameras as the imaging devices 60 and 130, it should understood that some embodiments may have only a single camera. Optionally, some embodiments may have an imaging device such as a camera at one angle and a machine code reader or similar non-photo-based data capture device at another angle. Although embodiments herein show that the image capture or data capture are aligned at orthogonally, it should be understood that alignment along other angles are also workable. Optionally, FIG. 12 also show that there may be one or more additional processor(s) on one or more assembly(s) 180 that may provide for on-board analytical capabilities to analyze the captured data and/or contain wired, wireless, or both types of communication hardware to transmit the data or an alert.

Sample Processing

Figure 14:
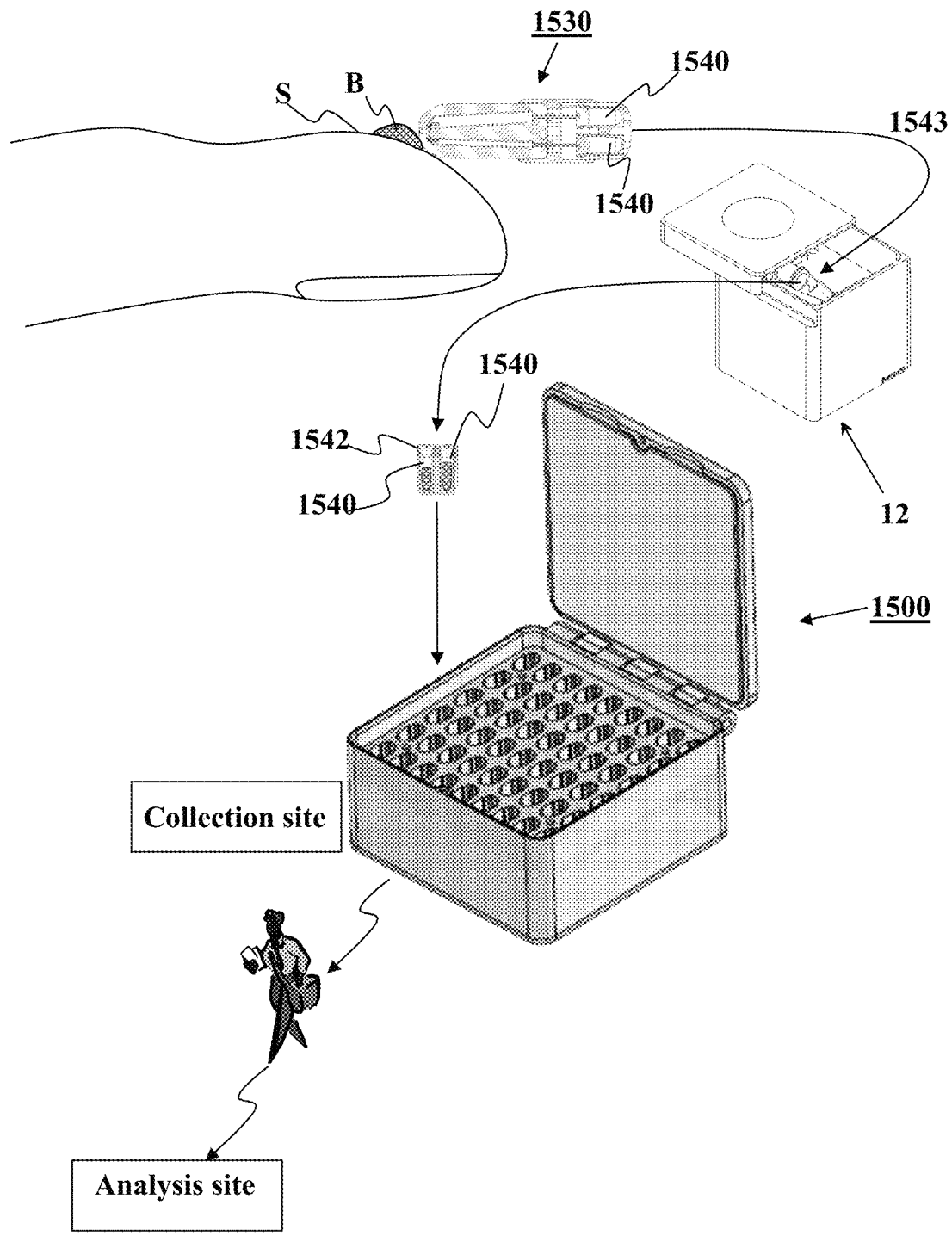
FIGS. 14 to 15 illustrate embodiments of methods including at least one embodiment of a device as disclosed herein.

Referring now to FIG. 14, one embodiment of bodily fluid sample collection and transport system will now be described. FIG. 14 shows a bodily fluid sample B on a skin surface S of the subject. In the non-limiting example of FIG. 14, the bodily fluid sample B can be collected by one of a variety of devices. By way of non-limiting example, collection device 1530 may be but is not limited to those described in U.S. Patent Application Ser. No. 61/697,797 filed Sep. 6, 2012, which is fully incorporated herein by reference for all purposes. In the present embodiment, the bodily fluid sample B is collected by one or more capillary channels and then directed into sample vessels 1540. The sample B forms through a wound that may be formed on the subject. This may be by way of fingerstick or wound created at other alternate sites on the body. A lancet, a needle, other penetrating device, or other technique may be used to release the bodily fluid sample from the subject. By way of non-limiting example, at least one of the sample vessels 1540 may have an interior that is initially under a partial vacuum that is used to draw bodily fluid sample into the sample vessel 1540. Some embodiments may simultaneously draw sample from the sample collection device into the sample vessels 1540 from the same or different collection channels in the sample collection device. Optionally, some embodiments may simultaneous draw sample into the sample vessels.

In the present embodiment after the bodily fluid sample is inside the sample vessels 1540, the sample vessels 1540 in their holder 1542 (or optionally, removed from their holder 1542) are placed in the sample verification device 12 as indicated by arrow 1543. Optionally, in some embodiments, the sample is centrifuged before or during image capture. Optionally, some other embodiments may use other formed component separation technique(s) currently known or developed in the future. The formed component separation technique may optionally be used before or during sample image capture. In this embodiment, the sample verification device may have a lid the closes over the sample vessels 1540 while they are processed. Optionally, some embodiments may not include a lid.

In the present embodiment after the sample verification is completed, the sample vessels 1540 in their holder 1542 (or optionally, removed from their holder 1542) are loaded into the transport container 1500. In this embodiment, there may be one or more slots sized for the sample vessel holder 1542 or slots for the sample vessels in the transport container 1500. By way of non-limiting example, they may hold the sample vessels in an arrayed configuration and oriented to be vertical or some other pre-determined orientation. It should be understood that some embodiments of the sample vessels 1540 are configured so that they hold different amount of sample in each of the vessels. By way of non-limiting example, this can be controlled based on the amount of vacuum force in each of the sample vessels, the amount of sample collected in the sample collection channel(s) of the collection device, and/or other factors. Optionally, different pre-treatments such as but not limited to different anti-coagulants or the like can also be present in the sample vessels.

As seen in FIG. 14, the sample vessels 1540 are collecting sample at a first location such as but not limited to a sample collection site. By way of non-limiting example, the bodily fluid samples are then transported in the transport container 1500 to a second location such as but not limited to an analysis site. The method of transport may be by courier, postal delivery, or other shipping technique. In many embodiments, the transport may be implemented by having a yet another container that holds the transport container therein. In one embodiment, the sample collection site may be a point-of-care. Optionally, the sample collection site is a point-of-service. Optionally, the sample collection site is remote from the sample analysis site.

Although the present embodiment of FIG. 14 shows the collection of bodily fluid sample from a surface of the subject, other alternative embodiments may use collection techniques for collecting sample from other areas of the subject, such as by venipuncture, to fill the sample vessel(s) 1540. Such other collection techniques are not excluded for use as alternative to or in conjunction with surface collection. Surface collection may be on exterior surfaces of the subject. Optionally, some embodiments may collect from accessible surfaces on the interior of the subject. Presence of bodily fluid sample B on these surfaces may be naturally occurring or may occur through wound creation or other techniques to make the bodily fluid surface accessible.

Figure 15:
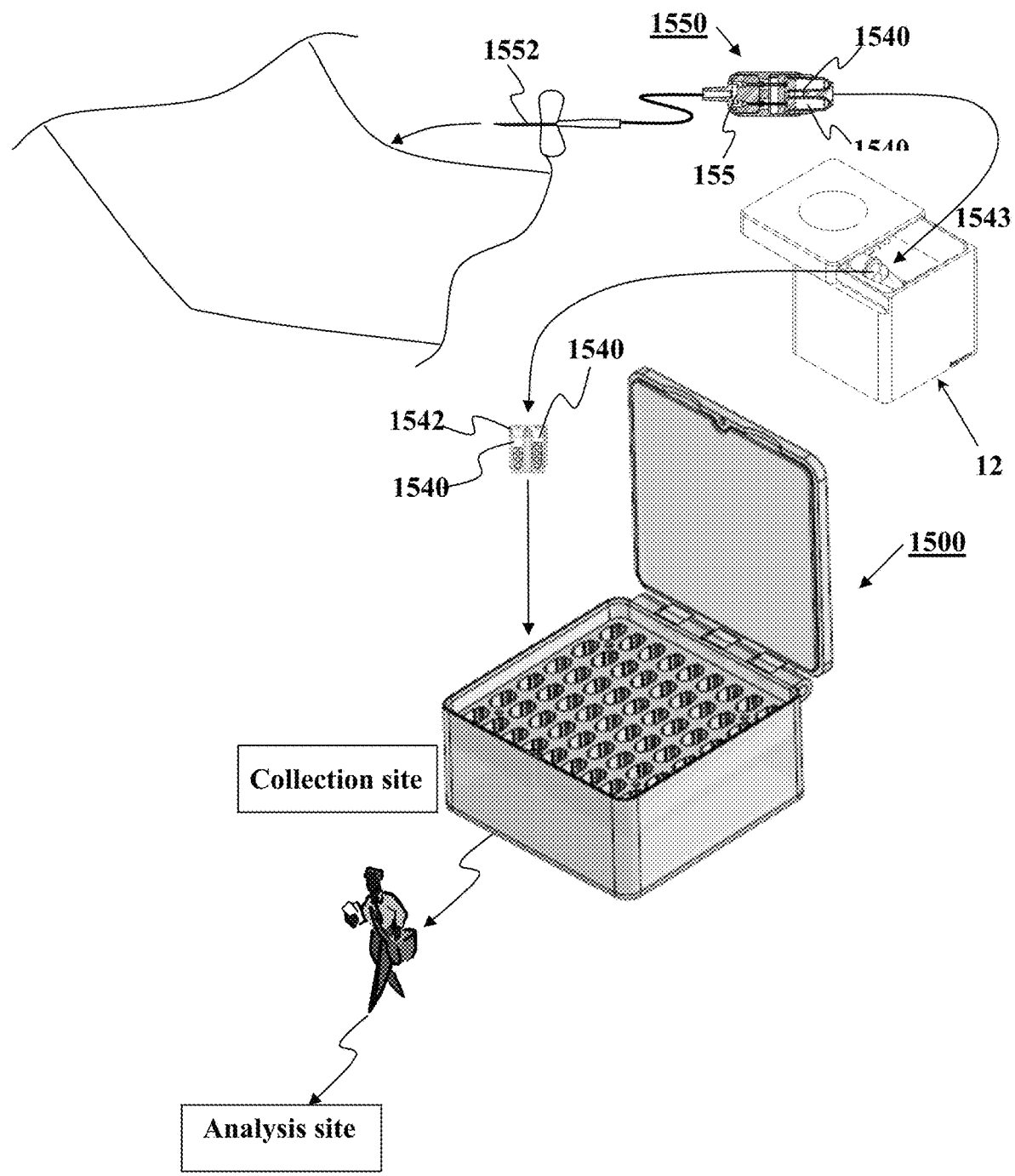

Referring now to FIG. 15, yet another embodiment is described herein wherein bodily fluid sample can be collected from an interior of the subject versus collecting sample that is pooled on a surface of the subject. This embodiment of FIG. 15 shows a collection device 1550 with a hypodermic needle 1552 that is configured to collect bodily fluid sample such as but not limited to venous blood. In one embodiment, the bodily fluid sample may fill a chamber 1554 in the device 1550 at which time sample vessel(s) 1540 may be engaged to draw the sample into the respective vessel(s). Optionally, some embodiments may not have a chamber 1554 but instead have very little void space other than channel(s), pathway(s), or tube(s) used to direct sample from the needle 1552 to the sample vessel(s) 1540. For bodily fluid samples such as blood, the pressure from within the blood vessel is such that the blood sample can fill the chamber 1554 without much if any assistance from the collection device. Such embodiments may optionally include one or more vents, such as but not limited to a port, to allow air escape as the channels in the collection device are filled with sample.

In the present embodiment after the bodily fluid sample is inside the sample vessels 1540, the sample vessels 1540 in their holder 1542 (or optionally, removed from their holder 1542) are placed in the sample verification device 12 as indicated by arrow 1543. In this embodiment, the sample verification device may have a lid the closes over the sample vessels 1540 while they are processed. Optionally, some embodiment may not include a lid.

In the present embodiment after the sample verification is completed, the sample vessels 1540 in their holder 1542 (or optionally, removed from their holder 1542) are loaded into the transport container 1500.

At least some or all of the embodiments can have a fill indicator such as but not limited to a view window or opening that shows when sample is present inside the collection device and thus indicate that it is acceptable to engage the sample vessel(s) 1540. Optionally, embodiments that do not have a fill indicator are not excluded. The filled sample vessel(s) 1540 may be disconnected from the sample collection device after a desired fill level is reached. Optionally, additional sample vessel(s) 1540 can be engaged to the sample collection device 1550 (or 1530) to collect additional amounts of bodily fluid sample.

In some embodiments, one or more cameras may be placed in the centrifuge rotor such that it can image the contents of the centrifuge vessel while the rotor is spinning. The camera images may be analyzed and/or communicated in real time, such as by using a wireless communication method. This method may be used to track the rate of sedimentation/cell packing, such as for the ESR (erythrocyte sedimentation rate) assay, where the speed of RBC (red blood cell) settling is measured. In some embodiments, one or more cameras may be positioned outside the rotor that can image the contents of the centrifuge vessel while the rotor is spinning. This may be achieved by using a strobed light source that is timed with the camera and spinning rotor. Real-time imaging of the contents of a centrifuge vessel while the rotor is spinning may allow one to stop spinning the rotor after the centrifugation process has completed, saving time and possibly preventing over-packing and/or over-separation of the contents.

Figure 17:
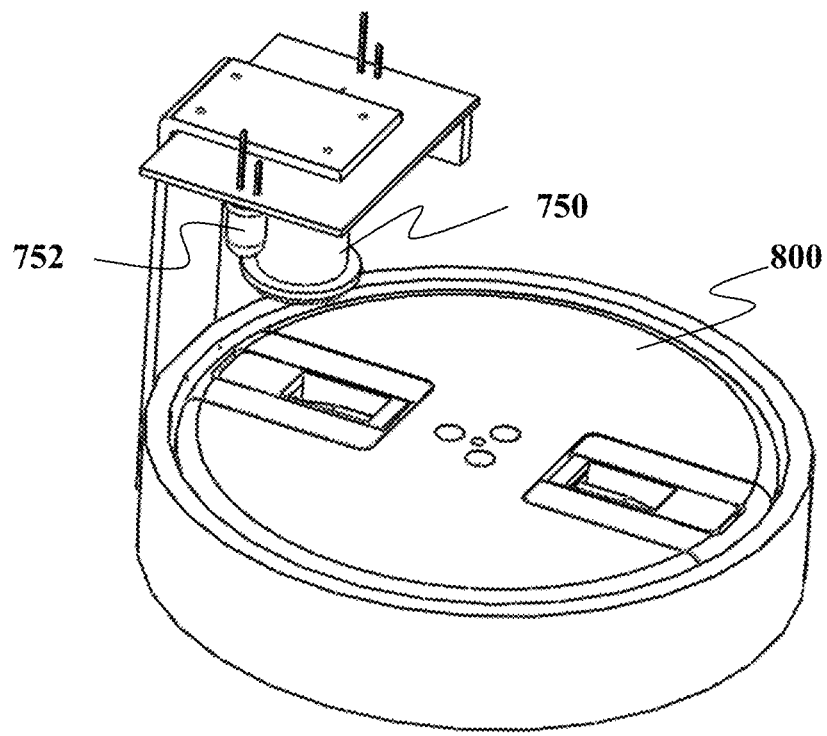
FIGS. 17 to 22 show other embodiments as described herein.

Referring now to FIG. 17, one embodiment of a centrifuge with a sample imaging system will now be described. FIG. 17 shows that, in some embodiments, the imaging device 750 such as but not limited to a camera, a CCD sensor, or the like may be used with a centrifuge rotor 800. In this example, the imaging device 750 is stationary while the centrifuge rotor 3800 is spinning. Imaging may be achieved by using a strobed light source that is timed with the camera and spinning rotor. Optionally, high speed image capture can also be used to acquire images without the use of a strobe.

Figure 18:
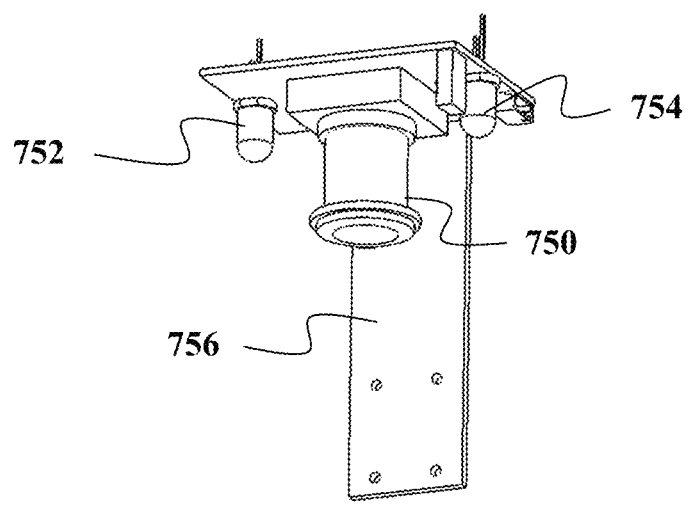

FIG. 18 shows one embodiment of the imaging device 750 that can be mounted in a stationary position to view the centrifuge vessel while it is spinning in the centrifuge. FIG. 18 shows that in addition to the imaging device 750, illumination source(s) 752 and 754 may also be used to assist in image capture. The mounting device 756 is configured to position the imaging device 750 to have a field of view and focus that enables a clear view of the centrifuge vessel and content therein. In one embodiment, the device 750 may function either like imaging device 60. Optionally, the device 750 may be used to function like detector 130 to detect identifier information from the sample vessel. The device 750 may be used to detect the identifier while the centrifuge is spinning. Optionally, the device 750 may be used in combination with the centrifuge rotor with integrated camera 800 to have at least a two detector system that can function similar to the multi-detector system shown in FIG.

9. FIG. 18 can be used to combine the detector capabilities of a device such as that of FIG. 9 with a centrifuge.

Figure 19:
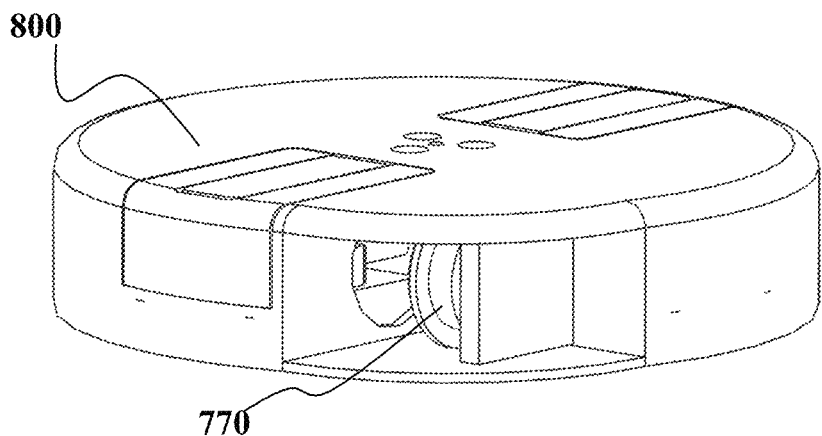
Figure 20:
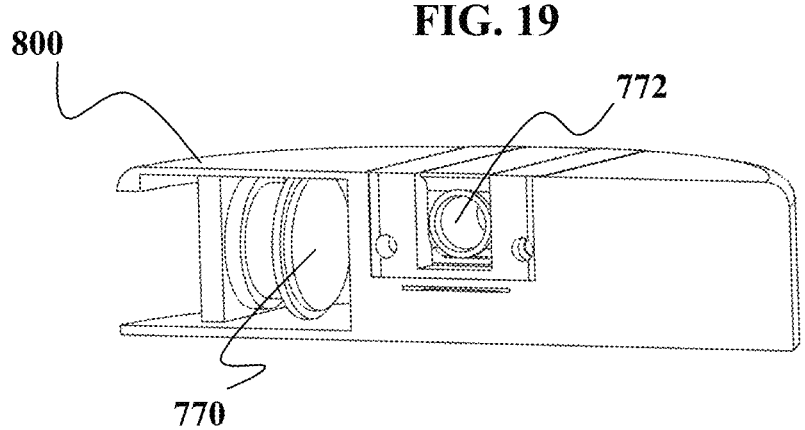
Figure 21:
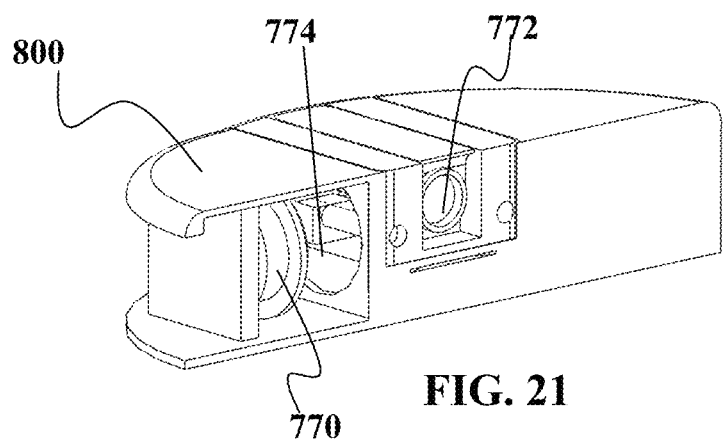

Referring now to FIGS. 19 to 21, yet another embodiment of a centrifuge with a sample imaging system will now be described in an integrated device. By way of non-limiting example, FIG. 19 can be used to combine the detector capabilities of a device such as that of FIG. 9 with a centrifuge. FIG. 19 shows that, in some embodiments, the imaging device 770 such as but not limited to a camera, a CCD sensor, or the like may be mounted inside or in the same rotation frame of reference as the centrifuge rotor 800. FIG. 20 shows a cross-sectional view showing that the imaging device 770 is positioned to view into the sample in the centrifuge vessel 772 through an opening 774 (shown in FIG. 21). Because the imaging system is in the centrifuge rotor 800, the imaging system can continuously image the centrifuge vessel 772 and the sample therein without the use of a strobe illumination system. Optionally, the centrifuge rotor 800 can be appropriately balanced to account for the additional weight of the imaging device 770 in the rotor. Optionally, some embodiments may combine both the embodiments of FIG. 18 with one of the embodiments from FIGS. 19 to 21 to combine the detector capabilities of a device such as that of FIG. 9 with a centrifuge. Optionally, still other detectors may be combined with a combined formed component separator and detector, such as but not limited one or more of a photodiode, a photomultiplier, a charge-coupled device (CCD), a spectrophotometer, a camera, a microscope, an absorbance detector, a turbidimeter, a color camera, an infrared detector, a non-visual wavelength detector, or other detector technology currently known or may be developed in the future.

Figure 22:
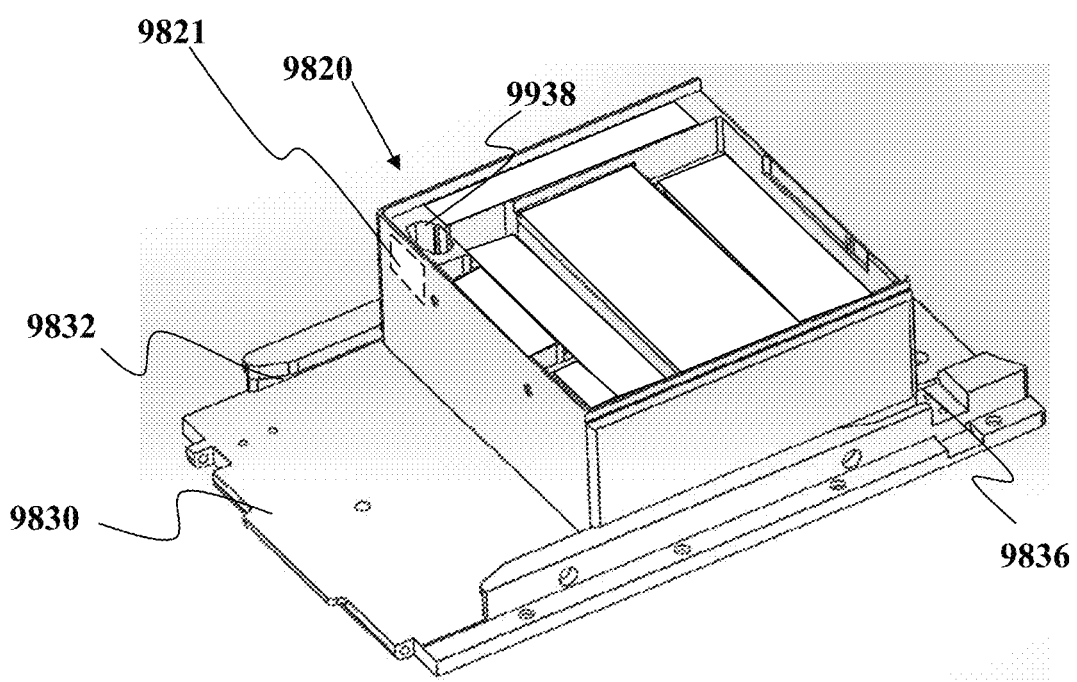

Referring now to FIG. 22, it should be understood that in some embodiments a cartridge 9800 may have at least one observation port, opening, transparent area, or other area 9821 that allows for interrogation of the sample vessel(s) that are held by cartridge 9800 that has at least some of the reagents and/or consumables to be used in assay performance. FIG. 22 shows one embodiment of a cartridge 9820 that is received into an assay station receiving location 9830 of the system such as but not limited to a sample processing device as described in U.S. patent application Ser. No. 13/769,820 filed Feb. 18, 2013 and fully incorporated herein by reference for all purposes. In some embodiments, an assay station receiving location may be a tray. In this non-limiting example, the assay station receiving location 9830 has slots 9832 that are shaped to receive rails 9834 on the cartridge 9820. The cartridge 9820 is inserted into the assay station receiving location 9830 until the cartridge 9820 engages a stop 9836. It should be understood that the regions in FIG. 22 and optionally in other cartridges described herein, the region may contain a plurality of wells, tips or the like such as shown in the cartridges of U.S. Pat. No. 8,088,593 fully incorporated herein by reference for all purposes.

Figure 23A:
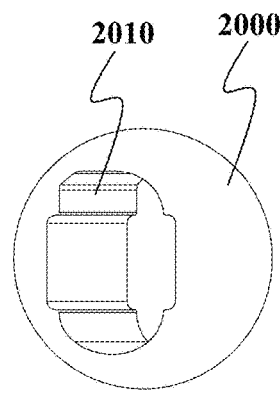
FIGS. 23A to 23D show various views of an adapter for a sample vessel(s) according to at least one embodiment as disclosed herein.
Figure 23B:
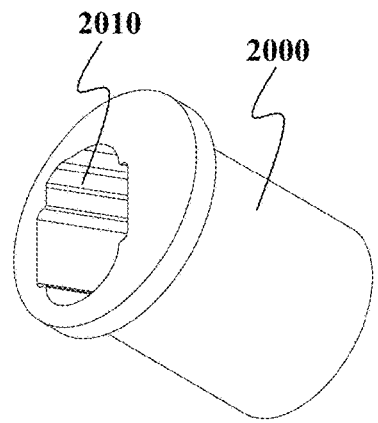
Figure 23C:
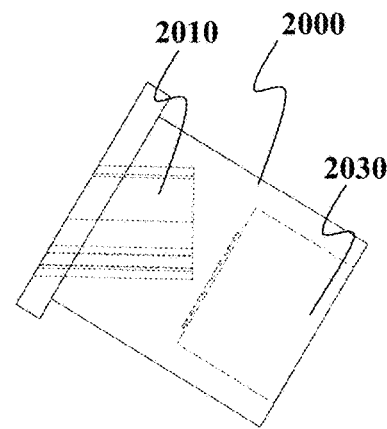

Referring now to FIGS. 23A to 23C, it should be understood that some embodiments herein may use an adapter 2000 to facilitate placement of a sample container into a formed component separation device such as but not limited to a centrifuge. Although this embodiment shows the adapter 2000 has a cylindrical shape conforming to the outline of the centrifuge vessel holder, it should be understood that other embodiments may configure the receiving location centrifuge vessel holder to be of different shapes. Some embodiments may have a receiving location which a top-down shape such as but not limited to square, rectangular, circular, oval, or the like and the adapter 2000 can be shaped to conform to that shape. Some embodiments may have an adapter with an outer perimeter shape that confirms to the shape presented at a receiver such as a centrifuge holder, but have an inner perimeter shape that is shaped to conform to that of the sample vessel(s).

As seen in FIG. 23C, the central axis of the cutout 2010 can be at an angle relative to the central axis of the insert 2000. Optionally, some embodiments may align these two axis to be parallel. Having the angled configuration for cutout 2010 can be beneficial to create a more horizontal orientation during centrifugation so that the meniscus of the packed formed components can have a more horizontal configuration (instead of angled) when the container is removed from adapter 2000 and the vessel is vertically oriented. In this manner, the meniscus will be perpendicular to a longitudinal axis of the vessel. This minimizes the risk of an inaccurate aspiration because of an angled meniscus causing an incomplete aspiration.

As seen in FIG. 23A, the cross-sectional shape of the cutout 2010 can be configured to match an outer perimeter shape of the sample vessel. It should be understood that in some embodiments, the material of adapter 2000 is transparent. Optionally, the material is a translucent material. Optionally, the sample vessel is one configured to be the same sample vessel that is used in sample collection so that there is no sample lost transferring the sample from a collection vessel to the centrifugation vessel. Herein, the shape of the cutout 2010 is designed to receive the collection vessel so that there is no loss simply to have the formed components separated. Herein, the shape of the cutout 2010 is designed to receive the collection vessel so that there is no loss simply to have the sample centrifuged. As seen in FIG. 23C, some embodiments may have a further hollowed-out area 2030.

Figure 23D:
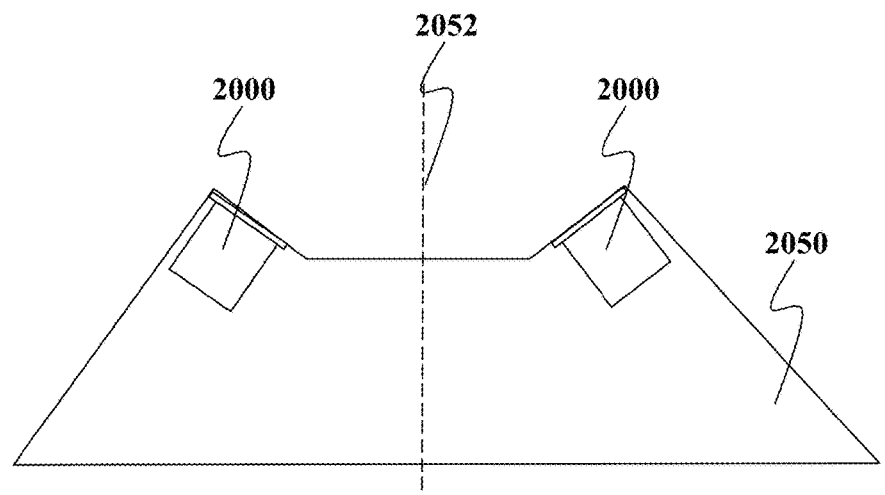

Referring now to FIG. 23D, a side cross-sectional view is shown of a centrifuge rotor 2050 having two adapters 2000 therein. In this embodiment, the centrifuge rotor 2050 rotates around a center axis 2052. The adapters 2000 in this embodiment slide into existing "slots" in the centrifuge rotor 2050 but will angle the vessels to be held in adapter 2000 to a desired orientation. Having the angled configuration for cutout 2010 in adapter 2000 can be beneficial to create a more horizontal orientation of vessel during centrifugation so that the meniscus of the liquid portion and the boundary of the formed components will both be perpendicular to a longitudinal axis of the vessel.

Use in the Field

In one non-limiting example, one or more purposes for the sample verification device can be to insure sample integrity prior to shipping or to insure sufficient sample is obtained prior to letting subject leave. For example, the sample verification can be helpful if an issue can be easily corrected by collecting another sample from the subject or through some other processing of the sample prior to shipment. Optionally, some embodiments may also include sample verification at the destination location of the sample.

In one non-limiting example, the sample verification device may be used at point-of-service locations in the field such as but not limited to retail store locations, pharmacies, private medical offices, doctor offices, end user homes, or other sites that may be remote from a clinical laboratory. Of course, some non-limiting examples may also use such sample verification devices at a clinical laboratory or a collection facility that is a part of a clinical laboratory and such use is not excluded. In one non-limiting example, the sample verification device is used to take images of samples after collection to determine sample volumes and other basic information about the sample before the sample is processed by clinical laboratory analysis hardware. This can help eliminate laboratory test error that results at the point of sample collection and unrelated to processing of the sample on the clinical laboratory analysis hardware. Although the embodiments herein are concerned primarily with human samples, it should be understood that sample from animals, samples from non-humans, and even non-biological samples can be used with one or more the sample verification devices herein.

In one non-limiting example, the sample verification device is used to take a photograph or digital image of a patient's blood sample at field locations. The sample verification device also reads one or more identifiers such as but not limited to a barcode, QR code, or other machine-readable non-letter type code on the sample container in order to identify the sample. In this non-limiting example, the image of the sample can be processed by a computer program to determine information about the sample including if enough volume of blood is present for successful testing. In embodiments, for example, the volume of the sample may be determined by detection of the upper surface of the volume of sample held in the container (e.g., by detection of light scattered from such a surface, or by detection of light intensity of color passing through the sample). In embodiments, for example, the volume of the sample may be determined by detection of the lower point within the sample container in which no sample is present (e.g., by detection of light intensity, or color, or light scattering, or other optical indication of the absence or presence of sample). In embodiments, for example, the volume of the sample may be determined by measurement of the volume of container in which sample is present, or in which sample is absent, e.g., by means indicated above, by detection of light passing through multiple portions of the container, or through substantially all of the container. If the sample is too small, the software can alert the technician that more blood must be drawn before the patient leaves the service center. The same image of the sample may also include information about the identifier(s).

Figure 16:
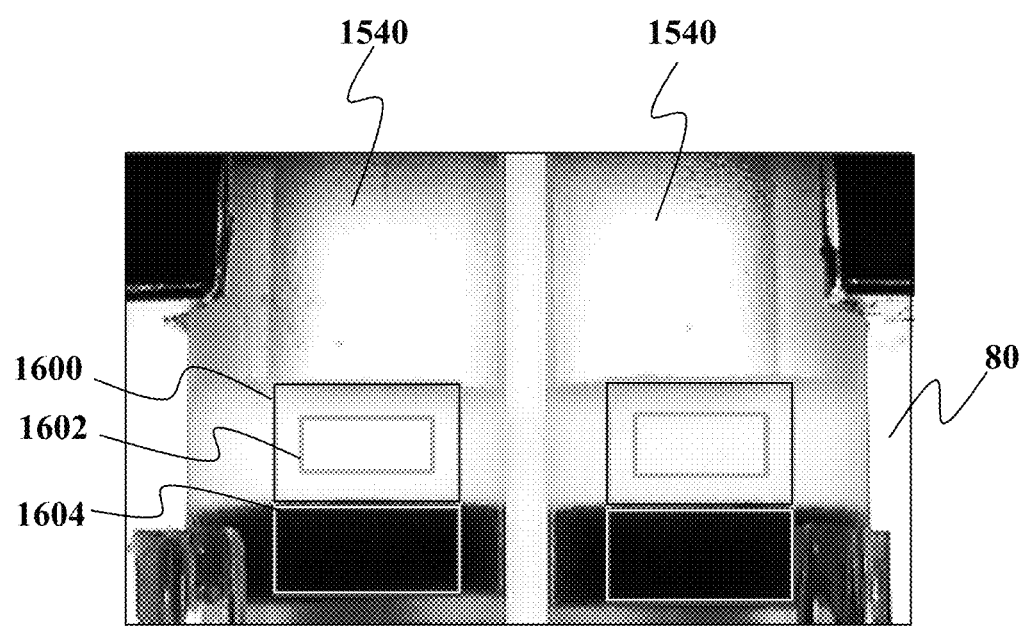
FIG. 16 shows a portion of an image of a sample according to at least one embodiment as disclosed herein.

Referring now to FIG. 16, by way of non-limiting example, one method of verifying the sample may be to inspect an image of the sample. Optionally, one method is to measure multiple wavelengths of light through absorbance or scattering. Optionally, some embodiments may use image analysis using pre-designated areas of interest 1600, 1602, 1604, or calculated areas of interest in the image of sample to detect any anomalies. Optionally, some embodiments may centrifuge the sample first and then during or afterwards, look for pellet and total volume. Optionally, after centrifuge or other formed component separation technique(s) currently known or may be developed in the future, the portion of the image to be verified is the liquid portion that is above a separator gel and/or the pellet of formed components that are at a bottom portion of the sample vessel in area of interest 1604. In one non-limiting example, the verification device can check for cell lysis by verifying the color of the liquid portion of the sample, such as in area of interest 1602. The color can be compared against calibrated colors deemed acceptable for plasma or similar liquid portion of the sample. Optionally, other sample quality issues such as foam on top, bubbles within the sample, or a non-horizontal meniscus in area of interest 1600. It should be understood that these areas of interests 1600, 1602, and 1604 are exemplary and non-limiting. Other embodiments herein may select other areas of interest or change the dimensions of the area of interest (wider, narrower, etc. . . . ).

In one non-limiting example, basic functionality of the sample verification device comprises two or more of the following: capture image(s) of at least one side of the sample container (for analysis) and the bottom of the sample container (for barcode identification) simultaneously and send the result to a separate computing device; have an average processing time of 30 seconds or less; provide backlighting of the sample container for a consistently well-lit image capture environment; block ambient light to reduce variance in images; sense if the lid is open or closed to reduce human error when using the device; use indicator lights to communicate the device's status to the user at all times; use data communication and/or power interface such as but not limited to a single micro USB input for both power and communication to/from the associated computer (it should be understood that future interfaces that satisfy the foregoing are not excluded); or have an anti-theft feature such as but no limited to a keyhole compatible with a standard Kensington laptop lock to prevent theft in the patient service center. In one embodiment, the overall geometry of the sample verification device may have at least two or more of the following: footprint no larger than about 6"×6"; height no taller than about 12"; weight no greater than about 5 kg. Internally, in one non-limiting example, the sample verification device is configured to have at least 0.5" of clearance on either side of the sample container when the sample container is inserted into the sample verification device.

In one non-limiting example, the camera used as the imaging device has at least two or more of the following: a minimum resolution of 1024×768 pixels; be powered and transmit data using at least USB 2.0 or higher; have the ability to take images within 2 seconds; or consume no more than 200 mA maximum. Optionally, some embodiments may communicate by way wireless protocol such as but not limited to Bluetooth LE, Bluetooth, 802.11 family of protocols, or other wireless data protocols. Some embodiments may also include cellular or other communications capability such as but not limited to 3G, 4G, 4GLTE, WiMax, or other current or future communication protocol. It should be understood that data transmission techniques such as those developed in the future may be adapted for use with the sample verification device and are not excluded herein.

In one non-limiting example, a backlight for use as source 80 has at least two or more of the following: an illuminated surface area of at least 20 mm×20 mm; substantially uniform illumination across its entire working surface area; consume no more than 100 mA maximum.

In one non-limiting example, the lid or other closeable portion of the sample verification device may have at least one lid position sensor having at least two or more of the following: detect when the lid is closed within no more than 0.25" of its fully closed position; relay the status of the door (open or closed) to a processor on the printed circuit assembly (PCA); consume no more than 30 mA maximum.

In one non-limiting example, the sample verification device may have a PCA with two or more of the following: monitor the status of the lid position sensor; have on/off control of the backlight; have control of visual displays such as but not limited to an LCD screen or visual indicators such as but not limited to RGB LED's to indicate device status; work as a USB pass-through for the two cameras; use USB 2.0 or higher USB protocol for both power and communication; allow for 24-hours of continuous use in any state without overheating or malfunctioning.

In at least one non-limiting example, the sample verification device can have at least two or more of the following: accommodate left and right handed users (such as through a center positioning of the sample holding area that does not bias either type of user); allow for use while wearing latex or other commonly used medical gloves wherein the use of buttons and other touch features on the device are not impaired by users that wear gloves; not damage the sample during use; allow for relatively easy cleaning of all potentially contaminated surfaces (e.g., by providing smooth surfaces and avoiding grooves and edges which may harbor contaminants); be composed of materials that are inert to the sample collection unit; be composed of materials that are easily cleaned in case of contamination from sample or user; be composed of materials that are durable; be absent of any sharp corners of edges that may exist from machining or any other reason. Optionally, the sample verification device may be configured to have a sample holder with recessed portions, fluid guides, overflow areas, or the like to move sample away from user contact areas in case of sample spillage or other undesired release.

It should be understood that some embodiments may use the sample verification device or portions of it as part of a system that may include a sample handling device, which is operably connected to sample verification device by a linkage effective that a sample (which may be a solid, fluid, gas, or other sample) is provided to the sample verification device in a form and configuration suitable for observation, measurement, or analysis by the sample verification device.

In embodiments, a sample handling device may include a linkage with the sample verification device, so that a separate linkage is not present, or is optional. A linkage of a sample handling device or a linkage may comprise, for example, a loading port or guide which aids in proper placement of a sample (or sample holder in which a sample may be retained or enclosed); or may comprise, for example, a mechanical system (e.g., a sample handling device) configured to transport a sample or sample holder from a first location to a second location, where the second location is a location within the sample verification device suitable for observation, measurement, or analysis of the sample; or may otherwise enable positioning of a sample or sample holder in a sample verification device for observation, measurement, or analysis.

In embodiments, a sample handling device may include, or may be a part of, or may operate in conjunction with, a fluid handling device or a fluid handling system. For example, a fluid handling device or system may be configured to transfer a sample, a sample holder, a reagent vessel, or other object or container to or within a sample verification device. In embodiments, a fluid handling device or system may comprise a pipette configured to uptake, dispense, or transfer a biological sample. A fluid handling device or system may include, or may be linked to, other components, devices, or systems. A fluid handling device or system may include a plurality of pipette heads (where an individual pipette head includes a pipette nozzle configured to connect with a pipette tip that is removable from the pipette nozzle); one or more plungers that are individually movable, wherein at least one plunger is within a pipette head and is movable within the pipette head; and a motor configured to effect independent movement of individual plungers of the plurality. In embodiments, a pipette nozzle may be configured to connect with, or may include, an actuator configured to effect independent movement of one or more individual plungers. In embodiments, a fluid handling device or system may be configured to engage, or may include, a sample holder; and at least one pipette head, wherein an individual pipette head comprises a pipette nozzle configured to connect with the sample holder that is removable from said pipette nozzle, wherein the apparatus is operably connected to an image capture device that is configured to capture an image within or through the sample holder. In one non-limiting example, after sample verification is confirmed, the sample may be fluidically removed from the sample container by way of a fluid handling device or a fluid handling system and transported onward without the sample container to other location(s) for aliquoting, dilution, or other further processing.

While the systems, devices, and methods have been described and illustrated with reference to certain particular embodiments thereof, those skilled in the art will appreciate that various adaptations, changes, modifications, substitutions, deletions, or additions of procedures and protocols may be made without departing from the spirit and scope of the invention. By way of non-limiting example, although at least some embodiments herein are shown as handling only a single sample container at a time, it should be understood that other embodiments can be configured to handle batches of sample containers simultaneously. Optionally, some embodiments may use a conveyor belt, a sequential loading system, or other multi-vessel transport to send a plurality of samples simultaneously, a plurality of samples sequentially, or a plurality of single samples in a sequential manner into the sample verification device.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

While at least some embodiments systems, devices, and methods have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for."

The invention claimed is:

1. A sample verification device for use with a sample container holding no more than 250 µL and containing at least one sample, the device comprising:
   an enclosure with a lid that is openable to allow for inserting said sample container, said enclosure providing a light controlled housing when the lid is closed and houses the following:
      at least one image capture device;
      at least another image capture device;
      a sample container support comprising a spacer with a cut-out for holding the sample container to be imaged along a first axis of said sample container by said at least one image capture device while also being imaged along a second axis by the at least another image capture device, wherein the second axis is orthogonal to the first axis;
      at least one backlight;

wherein said at least one image capture device is aligned to collect visual information about at least one characteristic of the sample and using image processing to detect if the sample fails to meet one or more sample collection criteria, wherein the sample container support is configured to position the sample container between said at least one backlight and the at least one image capture device, wherein the sample container is capped with an opaque container cap while the sample container is being imaged by said image capture device.

2. The sample verification device of claim 1 wherein a portion of said at least one image capture device is positioned below an upper plane of the spacer.

3. The sample verification device of claim 1 wherein a portion of said backlight is positioned below an upper plane of the spacer.

4. The device of claim 1 wherein said at least one image capture device simultaneously images all sample containers in the enclosure.

5. A sample verification device for use with a sample container containing at least one sample, the device comprising:
  an enclosure with a lid that is openable to allow for inserting said sample container, said enclosure providing a light tight enclosure when the lid is closed and houses the following:
  at least one image capture device;
  a sample container support;
  at least one backlight;
  wherein said at least one image capture device is aligned to collect visual information about at least one characteristic of the sample and using image processing to detect if the sample fails to meet one or more sample collection criteria, wherein the sample container support is configured to position the sample container between said at least one backlight and the at least one image capture device;
  a multi-angle information capture system comprising using the at least one image capture device and optical element to simultaneously image a first surface of the sample container and a second surface of the sample container, wherein said second surface is orthogonal to the first surface, wherein the sample container is capped with a non-transparent container cap while the sample container is being imaged by said image capture device.

6. The sample verification device of claim 1 further comprising a light controlled housing for containing at least a portion of the sample and at least a portion of the at least one image capture device.

7. The sample verification device of claim 6 wherein the light controlled housing comprises a portion movable from a closed position to an open position to allow for loading of the sample container into the sample verification device.

8. The sample verification device of claim 6 wherein a region of interest of the at least one image capture devices comprises portions of at least two sample containers.

9. The sample verification device of claim 6 wherein a region of interest of the at least one image capture devices simultaneously images a portion of the sample and a visual identifier on the sample container.

10. The sample verification device of claim 6 wherein a region of interest of the at least one image capture devices simultaneously images a portion of the sample container below an upper plane of the spacer.

11. The device of claim 5 wherein said at least one image capture device simultaneously images all sample containers in the enclosure.

12. A method of performing sample verification on a sample in a sample container, the method comprising:
  placing the sample container in an enclosure with a lid that is openable to allow for inserting said sample container, said enclosure containing a sample capture device and provides a light tight enclosure when the lid is closed;
  capturing information about at least one characteristic of the sample along a first axis of the sample container;
  capturing at least one sample identifier associated with the sample along a second axis of said sample container, wherein said second axis is orthogonal to the first axis, wherein said capturing occurs when the sample container is capped with a non-transparent container cap;
  keeping a subject at the sample collection facility until sample verification is completed;
  communicating an alert to a user if the sample fails to meet at least one sample collection criteria, whereby a remedial action is taken before the subject departs from the sample collection facility;
  wherein said capturing information comprises placing a sample vessel with the sample between a back light and an image capture device.

13. The method of claim 12, comprising placing the sample into a light-controlled imaging location.

14. The method of claim 12 wherein capturing comprises multi-axial imaging.

15. The method of claim 12 wherein capturing comprises multi-angle imaging.

16. The method of claim 12 wherein capturing comprises using a spacer to hold the sample container to allow for imaging along the first axis and the second axis.

17. The method of claim 12 wherein the sample capture device simultaneously images all sample containers in the enclosure.

* * * * *